United States Patent [19]

O'Doherty

[11] 4,265,901

[45] May 5, 1981

[54] 2-OXYBENZIMIDAZOLINE COMPOUNDS

[75] Inventor: George O. P. O'Doherty, Greenfield, Ind.

[73] Assignee: Eli Lilly and Company, Indianapolis, Ind.

[21] Appl. No.: 106,990

[22] Filed: Dec. 26, 1979

[51] Int. Cl.³ .................. A61K 31/415; A01N 43/52; C07D 235/26

[52] U.S. Cl. .................... 424/273 B; 71/92; 548/329; 548/332; 564/214

[58] Field of Search .................... 548/329; 424/273 B

[56] References Cited

U.S. PATENT DOCUMENTS

| Re. 20,508 | 1/1978 | O'Doherty | 71/88 X |
|---|---|---|---|
| 3,705,174 | 12/1972 | Fisher et al. | 548/329 |
| 3,813,407 | 5/1974 | O'Doherty | 548/329 X |
| 3,875,173 | 4/1975 | O'Doherty | 548/329 X |
| 3,980,784 | 9/1976 | Peterson | 424/273 |
| 3,989,840 | 11/1976 | O'Doherty | 424/300 |

OTHER PUBLICATIONS

Schipper, E., et al., in *Heterocyclic Compounds*, vol. 5, (Elderfield, editor), John Wiley, New York, 1957, p. 275.

Wright, J., *Chem. Rev.*, 48, 466–468 (1951).

Davey, R., et al., *The Southwestern Entomologist*, 4(4), 311–314 (1979).

Miesel, J., et al., manuscript submitted to J. Org. Chem., Jun. 1977.

*Primary Examiner*—Richard A. Schwartz
*Attorney, Agent, or Firm*—Kathleen R. S. Page; Arthur R. Whale

[57] ABSTRACT

The present invention is directed to 2-hydroxy- and 2-alkoxybenzimidazoline compounds which exhibit herbicidal, insecticidal, and ectoparasiticidal activity.

28 Claims, 4 Drawing Figures

2-OXYBENZIMIDAZOLINE COMPOUNDS

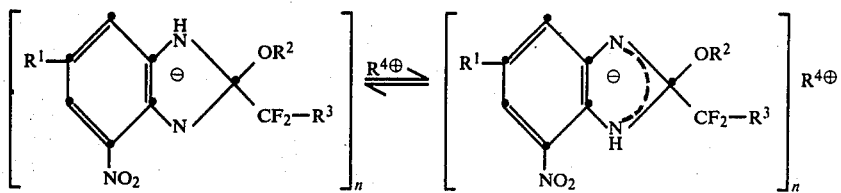

BRIEF SUMMARY OF THE INVENTION

The present invention is directed to 2-oxy-benzimidazoline compounds which exhibit herbicidal, insecticidal, and ectoparasiticidal activity.

DETAILED DESCRIPTION OF THE INVENTION

Figure 1:
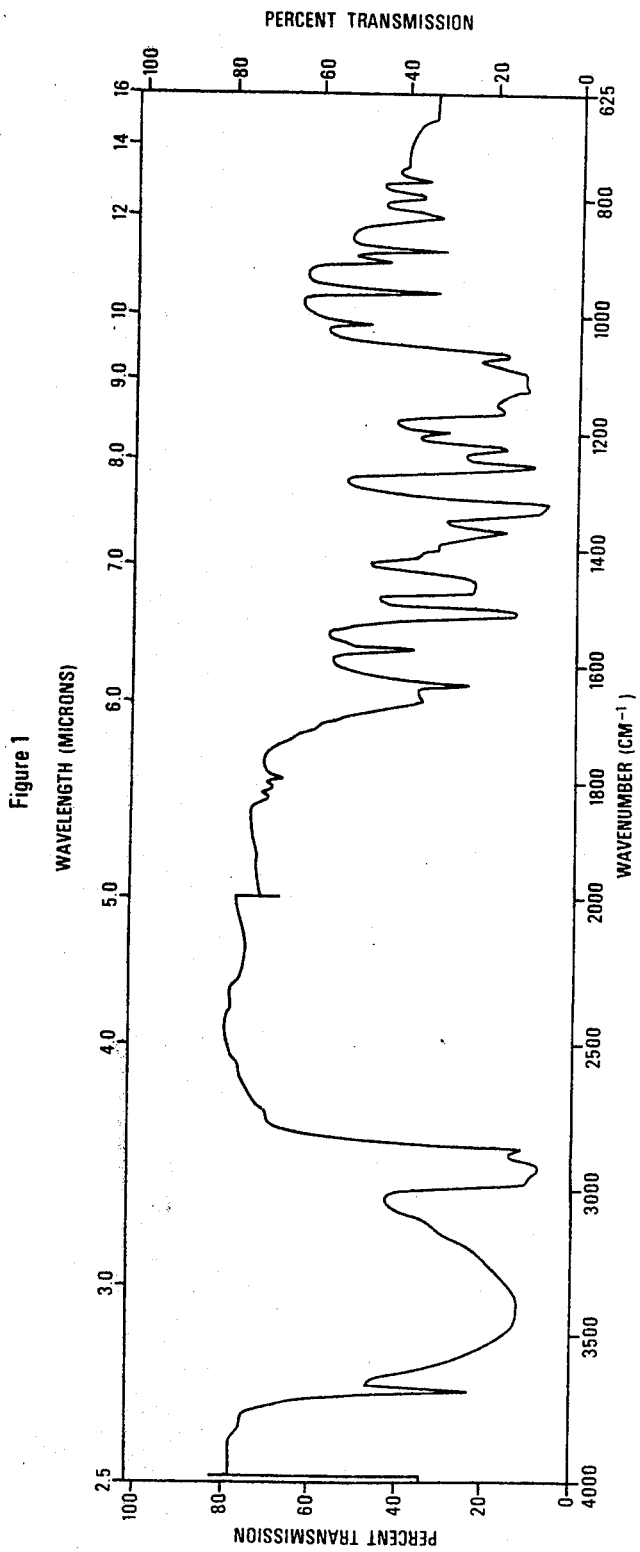
FIGS. 1–3 represent infrared spectra of a compound of the present invention, in two different forms, and of the corresponding dehydrobenzimidazole compound. The spectra are discussed further in Example 2.

The present invention is directed to compounds of the formula

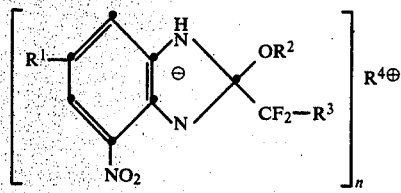   I wherein:
R$^1$ represents bromo, chloro, or trifluoromethyl;
R$^2$ represents hydrogen or loweralkyl of $C_1$–$C_4$;
R$^3$ represents hydrogen, fluoro, difluoromethyl, or trifluoromethyl;
R$^4$ represents sodium, potassium, lithium, silver, calcium, ammonium, or substituted ammonium derived from an organic amine which is as basic as, or more basic than, ammonia; and
n represents the valence of R$^4$; or a solvate thereof.

The present invention is also directed to the compound 1,2-dihydroxy-2-(1,1,2,2-tetrafluoroethyl)-4-nitro-6-(trifluoromethyl)benzimidazoline:

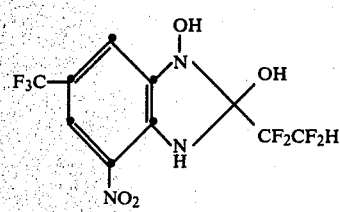

All of the compounds of the present invention exhibit herbicidal, insecticidal, and ectoparasiticidal activity.

The compounds of Formula I are portrayed as having a proton at the 1-position in the imidazole ring. As those skilled in the art will understand, the proton is in fact not restricted to either nitrogen The compounds of the present invention which are of Formula I are generally prepared by reacting a benzimidazole salt of the formula

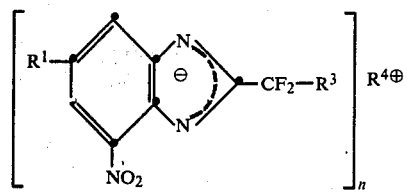

with a compound of the formula $R^2OH$. The conversion of the benzimidazole salt to the compound of the present invention goes forward readily at temperatures over a wide range, such as 0° to 150° C.; however, room temperatures are convenient. The amounts of reactants employed are not critical, although the reaction consumes equimolar amounts of the reactants. The reaction is conveniently conducted in a suitable solvent, typically an excess amount of the $R^2OH$ reactant.

The benzimidazole salt

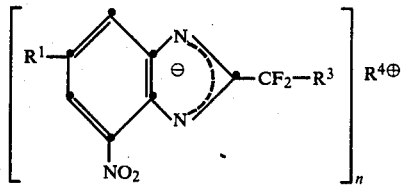

is itself readily prepared from the corresponding benzimidazole

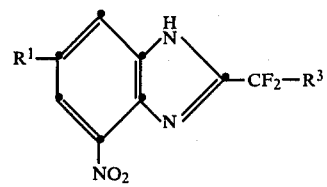

by treatment with appropriate base. Therefore, many of the present compounds are most conveniently prepared by reacting the latter compound with the $R^2OH$ reactant in the presence of base, whereby the present product is obtained with $R^4$=the cation of the base employed. The reaction conditions are the same as for the reaction of benzimidazole salt with $R^2OH$ reactant.

The latter benzimidazole compound is itself readily prepared from the corresponding $N^1$-(2,2-difluoroalkanoyl)-o-phenylenediamine of the formula

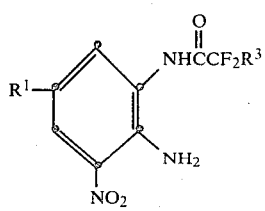

The cyclization of $N^1$-(2,2-difluoroalkanoyl)-o-phenylenediamine to benzimidazole occurs readily under basic conditions. Therefore, in another embodiment, the present compounds are prepared directly from the $N^1$-(2,2-difluoroalkanoyl)-o-phenylenediamines. In this embodiment the $N^1$-(2,2-difluoroalkanoyl)-o-phenylenediamine is reacted with the desired $R^2OH$ in the presence of base, whereby the product is obtained with $R^4 =$ the cation of the base employed. The reaction conditions are the same as for the reaction of benzimidazole or benzimidazole salt with $R^2OH$ reactant.

The foregoing procedures are generally suitable regardless of the salt ($R^4$) desired. However, it is sometimes preferred to prepare a given salt from another salt. Such conversion is carried out in conventional procedures.

The benzimidazole salts employed as starting materials to the present compounds are known compounds capable of including water of crystallization. That the present compounds are different compounds is established by infrared spectroscopy. The present compounds, unlike the corresponding dehydrobenzimidazole hydrates, give spectral evidence of an OH covalently bonded to carbon, as a sharp peak in the region of 3600–3700 cm.$^{-1}$ in the case of certain crystalline forms, and as a broad band in the region of 3300–3600 cm.$^{-1}$ in the instance of other crystalline forms. These are not seen in the spectra of the corresponding dehydrobenzimidazoles. Water of crystallization if present in either the claimed compounds or the dehydrobenzimidazoles is evidenced by a broad band centered about 3400 cm.$^{-1}$ and a medium band at about 1665 cm.$^{-1}$. Spectra on comparable prior art and claimed compounds are provided by the three drawings, which are discussed in Example 2.

In the substituted ammonium salts of the present invention, the identity of the organic amine is not critical so long as it is sufficiently basic. Any organic amine which is as basic as, or more basic than, ammonia, is satisfactory. Ammonia has a $K_b$ of $1.79 \times 10^{-5}$ (CRC Handbook of Chemistry and Physics, 56th Ed. (1975-6)); therefore, any organic amine of equal or stronger basicity is suitable. In general, the alkylamines, cycloalkylamines, alkylenepolyamines, aralkylamines, and heterocyclic amines are classes of compounds exhibiting adequate base strengths. Thus, representative bases include methylamine, dimethylamine, trimethylamine, methyldiethylamine, ethylamine, diethylamine, triethylamine, n-propylamine, di-n-propylamine, tri-n-propylamine, n-amylamine, cyclohexylamine, piperidine, pyrrolidine, N-methylpyrrolidine, diisopropylamine, ethylenediamine, tetramethylenediamine, ethanolamine, benzylamine, isobutylamine, di-n-butylamine, and the like.

The compound 1,2-dihydroxy-2-(1,1,2,2-tetrafluoroethyl)-4-nitro-6-(trifluoromethyl)benzimidazoline is prepared from 1-hydroxy-2-(1,1,2,2-tetrafluoroethyl)-4-nitro-6-(trifluoromethyl)benzimidazole:

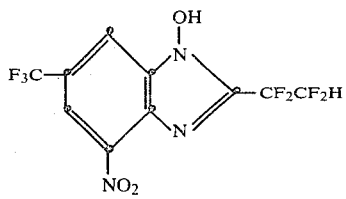

Typically, an alkaline solution of the compound is treated with excess acetic acid, precipitating the desired 1,2-dihydroxy-2-(1,1,2,2-tetrafluoroethyl)-4-nitro-6-(trifluoromethyl)benzimidazoline compound.

The 1-hydroxy-2-(1,1,2,2-tetrafluoroethyl)-4-nitro-6-(trifluoromethyl)benzimidazole starting material is readily prepared by the procedures of U.S. Pat. No. 3,875,173.

The following examples illustrate the synthesis of the compounds of the present invention.

EXAMPLE 1

Preparation of 2-Hydroxy-2-(1,1,2,2-Tetrafluoroethyl)-4-Nitro-6-(Trifluoromethyl)Benzimidazoline, Sodium Salt and Hydrate Thereof 3-Nitro-5-(trifluoromethyl)-$N^1$-(2,2,3,3-tetrafluoropropionyl)-o-phenylenediamine (35 grams) was dissolved in 100 ml. of N NaOH, and the solution was diluted to 331 ml. The reaction mixture was permitted to stand at room temperature for 24 hours. The solution, which was pale yellow, was then evaporated to a syrup, which was dissolved in diethyl ether and filtered. The filtrate was allowed to evaporate spontaneously at room temperature and a solid residue was obtained after 72 hours. It was ground up to give 35 grams of a yellow crystalline powder, melting over a wide range above 120° C.

A sample of 2-hydroxy-2-(1,1,2,2-tetrafluoroethyl)-4-nitro-6-(trifluoromethyl)benzimidazoline, sodium salt, prepared as described above, was dissolved in 150 ml. of diethyl ether, the solution was filtered, and 150 ml. of methylene chloride was added to the filtrate. The solvents were slowly distilled from the stirred crystalline solute mixture. The needles which had initially formed were replaced by a dense crystalline solid. It was filtered, washed with methylene chloride, and dried in vacuo at 40° C.

Calculated for $C_{10}H_5F_7N_3NaO_3=$C, 32.36; H, 13.6; N, 11.32; F, 35.83. Found: C, 32.52; H, 13.5; N, 11.37. F, 35.87.

EXAMPLE 2

Preparation of 2-Hydroxy-2-(1,1,2,2-Tetrafluoroethyl)-4-Nitro-6-(Trifluoromethyl)Benzimidazoline, Sodium Salt, and Hydrate 2-(1,1,2,2-Tetrafluoroethyl)-4-nitro-6-(trifluoromethyl)benzimidazole (40 grams) in acetone (200 mls.) was mixed with water (40 mls.) and sodium carbonate (10 grams). The reaction mixture was stirred under reflux for 2 hours. Additional sodium carbonate (100 grams) and diethyl ether (200 mls.) were added and the resulting mixture stirred 2 hours and filtered. The filtrate was evaporated to dryness in vacuo at 60° C. and the residual oil solidified to a crystalline solid.

It was analyzed by infrared spectroscopy; a copy of the spectrum, taken in Nujol, is reproduced herewith as FIG. 1. As can be noted on FIG. 1, the infrared spectrum of this product shows a peak at about 3690 cm$^{-1}$, indicating covalently bonded 2-hydroxy as either free OH stretching vibration or single bridge intramolecularly hydrogen bonded OH. The presence of water of crystallization is evidenced by a broad band centered at about 3400 cm$^{-1}$ and a small peak at about 1665 cm.$^{-1}$.

A 10-gram portion of this product was dissolved in 45 mls. of diethyl ether and 100 mls. of chloroform was added. The resulting slurry was distilled until no more water azeotroped. A dense crystalline solid precipitated and was separated by filtration.

Figure 2:
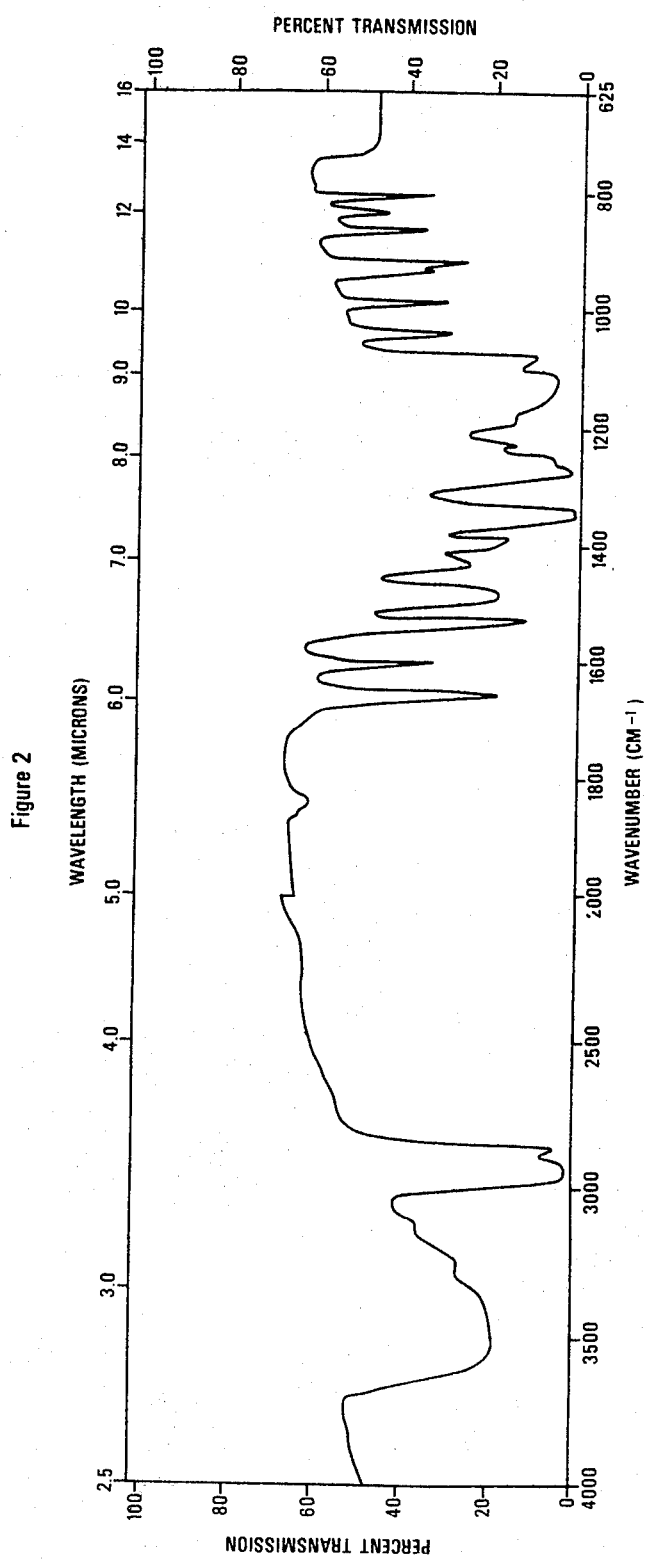

It was also analyzed by infrared spectroscopy and a copy of the spectrum is reproduced herewith as FIG. 2. As can be noted on FIG. 2, the infrared spectrum of this product, taken in Nujol, shows a broad band at about 3600 cm.$^{-1}$–3350 cm$^{-1}$, indicating covalently bonded OH intermolecularly hydrogen bonded in polymeric form. There is no evidence of water of crystallization.

Figure 3:
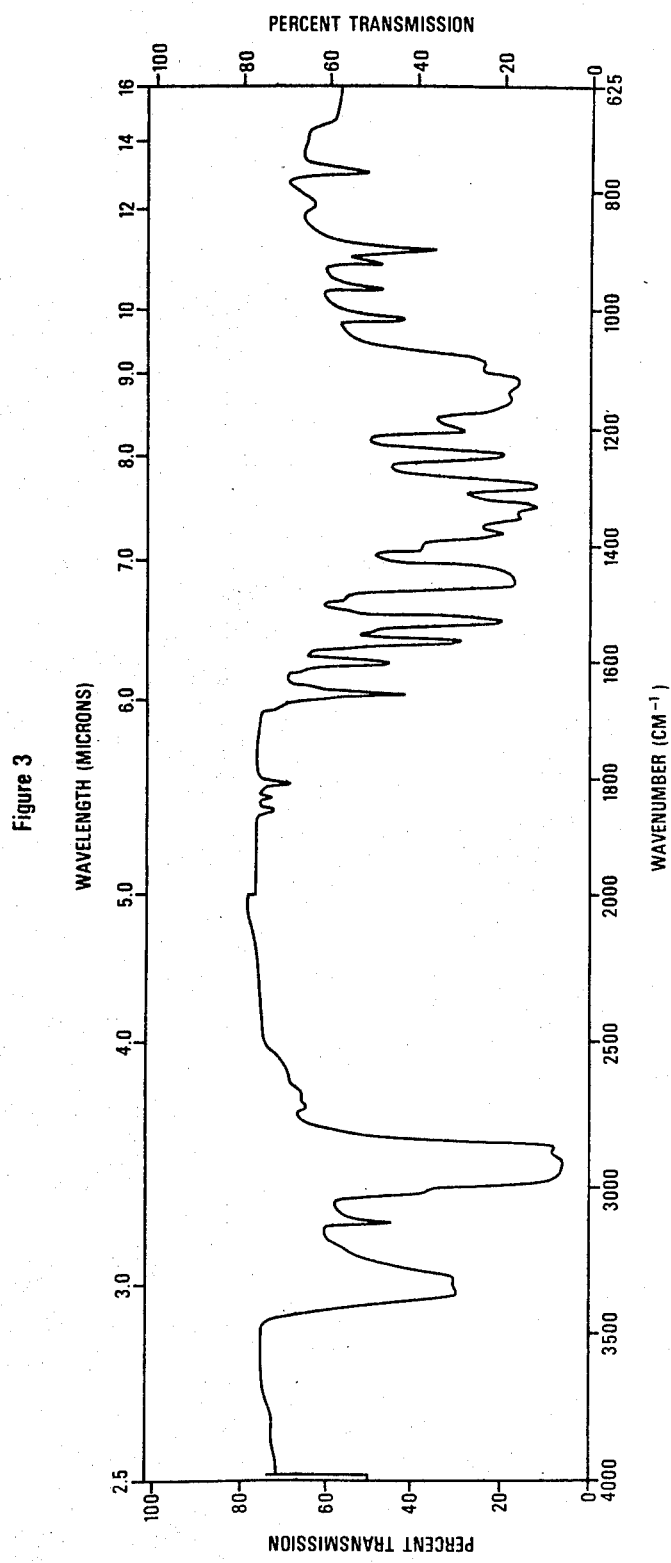

FIG. 3 represents the infrared spectrum of the corresponding dehydrobenzimidazole, 2-(1,1,2,2-tetrafluoroethyl)-4-nitro-6-(trifluoromethyl)benzimidazole. This spectrum shows only evidence of NH stretching, i.e., below 3500 cm$^{-1}$.

EXAMPLE 3

Preparation of
2-Hydroxy-2,6-Bis(Trifluoromethyl)-4-Nitrobenzimidazoline, Sodium Salt, Monohydrate 2,6-Bis(trifluoromethyl)-4-nitrobenzimidazole (29.9 grams) was mixed with 50 mls. of 2 N NaOH, and stirred until homogeneous. The initial volume of about 67 mls. was increased to 70 ml. by addition of distilled water. An 8 ml. portion was removed for ectoparasiticidal testing; the remaining 63 ml. portion was filtered and evaporated to dryness in vacuo. The resulting solid was allowed to stand overnight in air in a crystallizing dish, by which time the solid had taken on a crystalline lumpy appearance, apparently not hygroscopic. The solid was then ground to a powder, pale yellow in color, which melted at 140° C. to a glass. An IR spectrum taken in KBr showed a small band at about 1665 cm.$^{-1}$ and a broad band at about 3400 cm.$^{-1}$ indicative of water of crystallization. A sharp peak at about 3680 cm.$^{-1}$ established the presence of the 2-OH group; other peaks on the spectrum were confirmatory of the remainder of the structure. Elemental analysis showed:

Calc. for $C_9H_4F_6N_3O_3.H_2O.Na$: C, 31.12; H, 1.15; N, 12.10. Found: C, 30.47; H, 1.31; N, 12.23.

The product was thus established to be 2-hydroxy-2,6-bis(trifluoromethyl)-4-nitrobenzimidazoline, sodium salt, monohydrate.

EXAMPLE 4

Preparation of
2-Isopropoxy-2-(1,1,2,2-Tetrafluoroethyl)-4-Nitro-6-(Trifluoromethyl)Benzimidazoline, Potassium Salt 3-Nitro-5-(trifluoromethyl)-N$^1$-(2,2,3,3-tetrafluoropropionyl)-o-phenylenediamine (35 grams) and potassium carbonate (7 grams) were dissolved in 100 mls. of methanol and the solution refluxed for 16 hours, then evaporated to dryness in vacuo and the resulting solid heated at 100° C. in vacuo for 16 hours.

It was then dissolved in hot isopropanol (about 80° C.) and the solution was filtered and then cooled to room temperature. Crystals formed and were separated by filtration, washed with isopropanol and diethyl ether, and dried in vacuo at 50° C. for 2 hours. The product melted at 246°–248° C. and showed the following elemental analysis:

Calc. for $C_{13}H_{11}F_7KN_3O_3$: C, 36.37; H, 2.58; N, 9.37. Found: C, 36.13, H, 2.32; N, 9.85.

The identity of the product was further confirmed by NMR.

EXAMPLE 5

Preparation of
2-Hydroxy-2-(Difluoromethyl)-4-Nitro-6-Chlorobenzimidazoline, Calcium Salt 3-Nitro-5-chloro-N$^1$-(difluoroacetyl)-o-phenylenediamine (10 grams) and calcium hydroxide (10 grams) were refluxed in 200 grams of acetone for 2 hours. The reaction mixture was then filtered and evaporated. The residual oil was taken up in water, filtered, evaporated to 125 mls., and allowed to stand. The resulting crystalline precipitate was separated by filtration, m.p., 250° C. (dec.).

EXAMPLE 6

Preparation of
2-Hydroxy-2-(1,1,2,2-Tetrafluoroethyl)-4-Nitro-6-(Trifluoromethyl)Benzimidazoline, Calcium Salt A portion of 2-hydroxy-2-(1,1,2,2-tetrafluoroethyl)-4-nitro-6-(trifluoromethyl)benzimidazoline, sodium salt (3.73 grams) was dissolved in water and treated with an equivalent amount of calcium bromide. The solution was evaporated to dryness, and the residue was shaken with a small amount of water and filtered, leaving a yellow brown solid. It was dried in vacuo at 60° C. for 4 hours, then recrystallized from water, m.p. 210° C. (sinters).

EXAMPLE 7

Preparation of
2-Hydroxy-2-(1,1,2,2-Tetrafluoroethyl)-4-Nitro-6-(Trifluoromethyl)Benzimidazoline, Silver Salt In procedures similar to those reported in the preceding example, 2-hydroxy-2-(1,1,2,2-tetrafluoroethyl)-4-nitro-6-(trifluoromethyl)benzimidazoline sodium salt was reacted with silver nitrate, yielding 2-hydroxy-2-(1,1,2,2-tetrafluoroethyl)-4-nitro-6-(trifluoromethyl)-benzimidazoline, silver salt, as a white powder, m.p. >350° C.

EXAMPLE 8

Preparation of
2-Hydroxy-2-(1,1,2,2-Tetrafluoroethyl)-4-Nitro-6-(Trifluoromethyl)Benzimidazoline, Lithium Salt 3-Nitro-5-(trifluoromethyl)-N$^1$-(2,2,3,3-tetrafluoropropionyl)-o-phenylenediamine (35 grams) and lithium hydroxide (2.4 grams) were mixed in 200 mls. of water and stirred until homogeneous. The reaction mixture was allowed to stand until the color had faded to pale yellow, then evaporated to dryness in vacuo. Infrared spectroscopy showed an OH stretch above 3500 cm.$^{-1}$. The product was recrystallized from chloroform, m.p. 75° C. Elemental analysis showed Calc. for $C_{10}H_5F_7LiN_3O_3$: C, 33.82; H, 1.42; N, 11.83. Found: C, 32.20; H, 1.99; N, 11.32.

EXAMPLE 9

Preparation of
2-Hydroxy-2,6-Bis(Trifluoromethyl)-4-Nitrobenzimidazoline, Triethylammonium Salt 2,6-Bis(trifluoromethyl)-4-nitrobenzimidazole (5 grams) was mixed with 50 mls. of triethylamine and the mixture stirred for 90 minutes, then evaporated to dryness. The residual oil was dissolved in 30 mls. of water, filtered and allowed to evaporate spontaneously. The identity of the product was confirmed by infrared and NMR. Elemental analysis showed Calc. for $C_{15}H_{20}F_6N_4O_3$: C, 43.07; H, 4.84; N, 13.39. Found: C. 43.15; H, 4.52; N, 13.44.

EXAMPLE 10

Preparation of
2-Methoxy-2-(Pentafluoroethyl)-4-Nitro-6-(Trifluoromethyl)Benzimidazoline, Potassium Salt 2-(Pentafluoroethyl)-4-nitro-6-(trifluoromethyl)benzimidazole (3.28 grams) and potassium carbonate (0.7 gram) were refluxed in methanol (25 mls.). The refluxing was accompanied by stirring and was continued until the reaction mixture was homogeneous. A trace amount of potassium carbonate was filtered off. The filtrate was evaporated to a small volume, and allowed to stand. Crystals formed; they were separated by filtration, washed with methanol, and air dried for 30 minutes.

EXAMPLE 11

Preparation of
2-Ethoxy-2-Difluoroethyl-4-Nitro-6-Chlorobenzimidazoline, Potassium Salt $N^1$-(Difluoroacetyl)-3-nitro-5-chloro-o-phenylenediamine (5.0 grams) and potassium carbonate (5 grams) were refluxed in ethanol (100 mls.), with stirring, for five hours. The reaction mixture was then filtered and evaporated to dryness at 100° C. The residue was taken up in ethanol (20 mls.) and allowed to stand, depositing crystals. The crystals were separated by filtration, m.p. 115°–125° C. NMR confirmed the identity of the product.

EXAMPLE 12

Preparation of
1,2-Dihydroxy-2-(1,1,2,2-Tetrafluoroethyl)-4-Nitro-6-(Trifluoromethyl)Benzimidazoline A mixture of N-(2,2,3,3-tetrafluoropropionyl)-2,6-dinitro-4-(trifluoromethyl)aniline (20 grams), 200 ml. of ethanol, and 1.5 grams of 5 percent palladium on carbon was hydrogenated to 137 lbs. TLC showed three streaks. The solution was left standing for 1½ hours, after which the expected product streak predominated. The reaction mixture was hydrogenated further (8 more lbs) then left standing another 20 minutes. The reaction mixture was then filtered and evaporated, leaving 17.8 grams of an orange solid. It was dissolved in about 75 ml. of water and 2.1 grams of NaOH, filtered, and acidified with slow dropwise addition of about 10 ml. of acetic acid in about 50 ml. of water. At about pH 5-6, a glob of sticky dark material coagulated onto the stirrer and was removed. The acidification was continued, yielding a flocculant precipitate which was separated by filtration and air dried. It was purified by dissolving it in a small amount of 1 percent NaOH solution and reacidifying with dilute acetic acid, yielding the expected product as a pale yellow solid which on rapid heating melted sharply at about 100° C., resolidified, and melted again at 216°–219° C.

The filtrate from the large scale acidification was extracted with diethyl ether, evaporated, dissolved in 1% NaOH, acidified with glacial acetic acid, and filtered; the resulting product was tested for its herbicidal and insecticidal activities, as reported hereinbelow.

Figure 4:
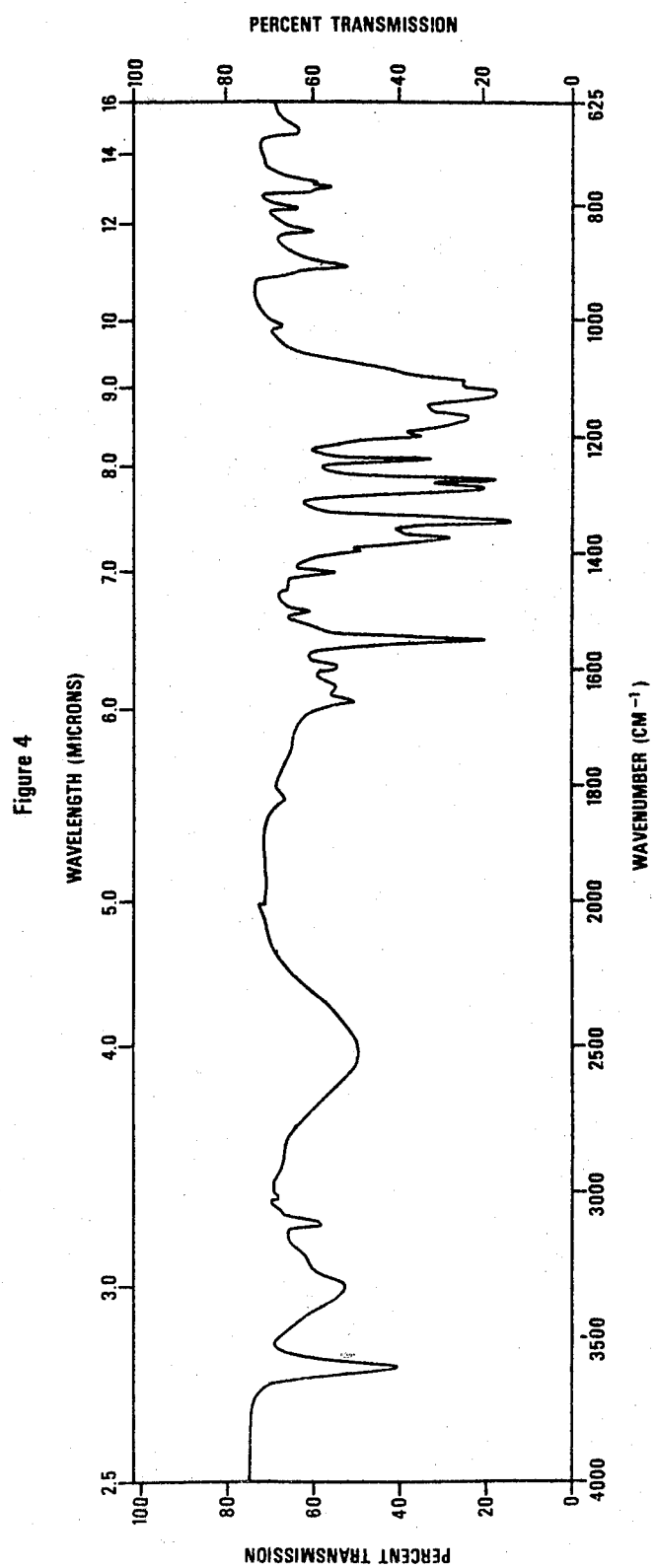
FIG. 4 represents the infrared spectrum of the compound of Example 12.

The infrared spectrum of the compound, taken in KBr, is reproduced as FIG. 4.

Other representative compounds of the present invention include the following:

2-hydroxy-2-(1,1,2,2-tetrafluoroethyl)-4-nitro-6-(trifluoromethyl)benzimidazoline, potassium salt 2-hydroxy-2-(1,1,2,2-tetrafluoroethyl)-4-nitro-6-(trifluoromethyl)benzimidazoline, ammonium salt 2-hydroxy-2-(1,1,2,2-tetrafluoroethyl)-4-nitro-6-(trifluoromethyl)benzimidazoline, triethylammonium salt 2-hydroxy-2-(1,1,2,2-tetafluorethyl)-4-nitro-6-(trifluoromethyl)benzimidazoline, pyridinium salt 2-hydroxy-2-(1,1,2,2-tetrafluoroethyl)-4-nitro-6-(trifluoromethyl)benzimidazoline, morpholinium salt 2-hydroxy-2-(1,1,2,2-tetrafluoroethyl)-4-nitro-6-(trifluoromethyl)benzimidazoline, piperidinium salt 2-hydroxy-2-(1,1,2,2-tetrafluoroethyl)-4-nitro-6-(trifluoromethyl)benzimidazoline, methylammonium salt 2-hydroxy-2-(1,1,2,2-tetrafluoroethyl)-4-nitro-6-bromobenzimidazoline, sodium salt 2-hydroxy-2-(1,1,2,2-tetrafluoroethyl)-4-nitro-6-chlorobenzimidazoline, sodium salt 2-hydroxy-2-(1,1,2,2-tetrafluoroethyl)-4-nitro-6-chlorobenzimidazoline, potassium salt 2-hydroxy-2-(1,1,2,2-tetrafluoroethyl)-4-nitro-6-chlorobenzimidazoline, ammonium salt 2-hydroxy-2,6-bis(trifluoromethyl)-4-nitrobenzimidazoline, potassium salt 2-hydroxy-2,6-bis(trifluoromethyl)-4-nitrobenzimidazoline, ammonium salt 2-hydroxy-2-(pentafluoroethyl)-4-nitro-6-(trifluoromethyl)benzimidazoline, sodium salt 2-hydroxy-2-(pentafluoroethyl)-4-nitro-6-(trifluoromethyl)benzimidazoline, potassium salt 2-hydroxy-2-(pentafluoroethyl)-4-nitro-6-(trifluoromethyl)benzimidazoline, ammonium salt 2-hydroxy-2-(1,1,2,2-tetrafluoroethyl)-4-nitro-6-(trifluoromethyl)benzimidazoline, potassium salt, monohydrate 2-hydroxy-2-(1,1,2,2-tetrafluoroethyl)-4-nitro-6-(trifluoromethyl)benzimidazoline, ammonium salt, monohydrate 2-methoxy-2,6-bis(trifluoromethyl)-4-nitrobenzimidazoline, sodium salt 2-ethoxy-2,6-bis(trifluoromethyl)-4-nitrobenzimidazoline, triethylammonium salt 2-hydroxy-2-(1,1,2,2-tetrafluoroethyl)-4-nitro-6-chlorobenzimidazoline, sodium salt Preferred compounds are those wherein $R^1$=chloro or trifluoromethyl, especially trifluoromethyl; $R^2$=H; $R^3$=fluoro or difluoromethyl, especially difluoromethyl; n=1; and $R^4$=sodium, potassium, or ammonium. An especially preferred compound is 2-hydroxy-2-(1,1,2,2-tetrafluoroethyl)-4-nitro-6-(trifluoromethyl)benzimidazoline, sodium salt, or a hydrate thereof.

The compounds of the present invention exhibit herbicidal activity and can be employed to control the growth of unwanted vegetation. Herbicidal activity is exhibited at application rates of from about 0.1 to about 8 or more pounds per acre. The compounds of the present invention also exhibit insecticidal activity and can be employed for the control of various insect species. With proper selection of rates to avoid phytotoxicity, the compounds can be employed for the control of insect species on plant crops. In general, insecticidal action is exhibited by liquid formulations containing the present compounds at concentrations of from 10 to 100 ppm.

For either herbicidal or insecticidal application, the compounds can be formulated in methods known in the art of agricultural chemicals. Typically, the compound of choice is mixed with an agriculturally acceptable adjuvant, which can be a solvent, an inert diluent, a surface active agent, or the like.

In one embodiment, the compound of choice is formulated with an inert carrier and a surface active agent to constitute a wettable powder formulation; this formulation can be added to water to constitute an ultimate treating formulation. The present compound can also be mixed with a water-immiscible solvent and a surface active agent, to serve as an emulsifiable concentrate which can be diluted with water to obtain an ultimate treating formulation. In view of the water solubility of the present compounds, many are satisfactorily formulated simply as a water soluble concentrate comprising compound and a surface-active agent. Many other conventional techniques are known to those skilled in the art and can be employed in formulating the compounds of the present invention.

The following examples illustrate the herbicidal and insecticidal action of the compounds of the present invention.

EXAMPLE 13

Evaluation of Compounds as Herbicides

In this evaluation, each compound to be tested was dissolved in a 1:1 mixture of acetone and ethanol containing a small amount of Toximul R and Toximul S (each a sulfonate/nonionic blend produced by Stepan Chemical Company, Northfield, Illinois). The solution was then diluted with deionized water to a composition of the following concentrations, by weight:

| | | |
|---|---|---|
| test compound | 0.5% | |
| acetone | 4.0% | |
| ethanol | 4.0% | |
| Toximul R&S | 0.1% | |
| deionized water | 91.4% | |
| | 100% | |

Plant species used as indicators of herbicidal activity were planted in galvanized pans (flats) 31.5 cm. long, 21.5 cm. wide, and 8.0 cm. deep. The bottoms of the flats had holes to facilitate drainage. The soil used was a 1:1 ratio by volume of masonry sand and shredded top soil.

The planting procedure began by filling a flat two-thirds full with sterilized soil. The soil was then leveled and tamped.

Seeds of seven indicator species were planted in rows perpendicular to the long axis of the flat, one species per row, and covered with 0.5 to 1.0 cm. of sterilized soil. Indicator species and approximate number of seeds planted were as follows:

Corn (*Zea mays*) 4
Crabgrass, Large (*Digitaria sanguinalis*) 100
Foxtail Millet (*Setaria italica*) 100
Morning glory (*Ipomoea purpurea*) 15
Pigweed (*Amaranthus retroflexus*) 150
Velvetleaf (*Abutilon theophrasti*) 50
Zinnia (*Zinnia elegans*) 20

Flats that were to receive preemergence treatments were planted one day prior to, or on the same day treatments were applied. Flats that were to receive postemergence treatments were planted 9 days prior to treatment and placed in a growth chamber until the day of treatment. In the growth chamber, flats received 12 to 18 hours of light per day and were subject to temperatures of 75° to 85° F.

The formulated test compound was applied uniformly to the indicator species with a modified DeVilbiss atomizer using air pressure of 3 to 5 psi. Each flat received 12.5 ml. of spray solution which was equal to 200 gallons/acre total spray volume. Plants were maintained in a greenhouse after treatment.

Herbicidal effects of chemicals were evaluated by two injury rating systems 18 days after preemergence applications and 14 days after postemergence applications. The degree of plant injury was based on a 1 to 5 scale and a single numerical rating was assigned to each test species as follows:

1=no injury
2=slight injury
3=moderate injury
4=severe injury
5=death

The type of injury was also classified and recorded on the test result sheet. One or more of the following types of injury were assigned to each indicator species.

A=Abscission of leaves
B=Burned
C=Chlorosis
D=Death
E=Epinasty
F=Formative effects other than epinasty
G=Dark green
I=Increased plant growth
L=Local necrosis
N=No germination
P=Purple pigmentation
R=Reduced germination
S=Stunting
U=Unclassified injury The results of these evaluations are set forth in the following tables. In this and in following tables, dashes indicate that no evaluation was made.

| | | | | | | | | | | | |
|---|---|---|---|---|---|---|---|---|---|---|---|
| | | | | PRE-EMERGENCE | | | | | | | |
| Compound of Example No. | Rate of Appln. lb./A | Corn | Cotton | Soybean | Wheat | Alfalfa | Sugar Beet | Rice | Cucumber | Tomato | Barnyard Grass |

-continued

PRE-EMERGENCE

| Compounds of Example No. | Rate of Appln. lb./A | Lambs-quarter | Large Crabgrass | Mustard | Pigweed | Foxtail | Wild Oat | Velvetleaf | Jimsonweed | Morning-glory | Zinnia |
|---|---|---|---|---|---|---|---|---|---|---|---|
| 2 | 8 | 3SB | — | — | — | — | — | — | — | — | — |
| 2 | 4 | 1 | 2B | 2B | 3BS | 5N | 5N | 2SB | 4BS | 4BS | 2BS |
| 2 | 2 | 1 | 1 | 1 | 1 | 5D | 5D | 2S | 1 | 1 | 1 |
| 2 | 1 | 1 | 2B | 1 | 1 | 2SB | 2S | 1 | 1 | 1 | 1 |
| 2 | 1 | 1 | 1 | 1 | 1 | 1 | 3SR | 1 | 1 | 2S | 2S |
| 2 | ½ | 1 | 1 | 1 | 1 | 3SR | 2S | 1 | 1 | 2S | 1 |
| 2 | ¼ | 1 | 1 | 1 | 1 | 1 | 1 | 1 | 1 | 1 | 1 |
| 5 | 8 | 1 | — | — | — | — | — | — | — | — | — |
| 12 | 8 | 1 | — | — | — | — | — | — | — | — | — |
| 12 | 2 | 1 | 1 | 1 | 1 | 3SB | 3S | 1 | 1 | 1 | 1 |
| 12 | 1 | 1 | 1 | 1 | 1 | 1 | 1 | 1 | 1 | 1 | 1 |
| 12 | ½ | 1 | 1 | 1 | 1 | 1 | 1 | 1 | 1 | 1 | 1 |

| Compounds of Example No. | Rate of Appln. lb./A | Lambs-quarter | Large Crabgrass | Mustard | Pigweed | Foxtail | Wild Oat | Velvetleaf | Jimsonweed | Morning-glory | Zinnia |
|---|---|---|---|---|---|---|---|---|---|---|---|
| 2 | 8 | — | 5N | — | 5D | 5N | — | 5D | — | 5N | 5D |
| 2 | 4 | 5D | 4RS | 5D | 4RS | 2S | 5 | 4BS | 5D | 4BS | 4BS |
| 2 | 2 | 5D | 4RS | 5D | 4SR | 2S | 2 | 2S | 3BS | 2B | 2S |
| 2 | 1 | 4B | 3S | 4B | 3S | 1 | 1 | 1 | 1 | 1 | 1 |
| 2 | 1 | 4SR | 2S | 4B | 1 | 1 | 1 | 1 | 1 | 1 | 1 |
| 2 | ½ | 2S | 1 | 2S | 2S | 1 | 1 | 1 | 1 | 1 | 1 |
| 2 | ¼ | 1 | 1 | 1 | 1 | 1 | 1 | 1 | 1 | 1 | 1 |
| 5 | 8 | — | 3RS | — | 2S | 3R | — | 3RS | — | 3RS | 4R |
| 12 | 8 | — | 4RS | — | 5N | 2S | — | 3BS | — | 3BS | 4RS |
| 12 | 2 | 3S | 4SB | 2S | 4S | 1 | 2B | 1 | 1 | 1 | 1 |
| 12 | 1 | 3SB | 2S | 1 | 3S | 1 | 1 | 1 | 1 | 1 | 1 |
| 12 | ½ | 1 | 1 | 1 | 1 | 1 | 1 | 1 | 1 | 1 | 1 |

POST-EMERGENCE

| Compound of Example No. | Rate of Appln. lb./A | Corn | Large Crabgrass | Pigweed | Foxtail | Velvetleaf | Morning-glory | Zinnia |
|---|---|---|---|---|---|---|---|---|
| 2 | 8 | 5D | 5D | 5D | 5D | 5D | 5D | 5D |
| 2 | 4 | 3BS | 5D | 5D | 4BS | 5D | 4BS | 5D |
| 2 | 2 | 3BS | 5D | 5D | 4BS | 5D | 3BS | 5D |
| 2 | 1 | 2B | 4BS | 5D | 4BS | 3BS | 3B | 4B |
| 2 | 1 | 2SB | 4BS | 5D | 4BS | 4BS | 3BS | 4BS |
| 2 | ½ | 1 | 3BS | 4BS | 3BS | 2SB | 2B | 3BS |
| 2 | ¼ | 1 | 2BS | 3BS | 3BS | 2B | 2B | 3BS |
| 5 | 8 | 5D | 4BS | 4BS | 5D | 5D | 4BS | 5D |
| 5 | 4 | 4BS | 4BS | 3BS | 3BS | 4BS | 3BS | 4BS |
| 5 | 2 | 2B | 3BS | 3BS | 4BS | 3BS | 2BS | 3BS |
| 5 | 1 | 1 | 3BS | 2S | 4BS | 3BS | 2BS | 3BS |
| 12 | 8 | 1 | 3BS | 5D | 3BS | 4BS | 2B | 4BS |
| 12 | 2 | 2B | 5D | 5D | 4BS | 4BS | 3BS | 5D |
| 12 | 1 | 1 | 5D | 5D | 4BS | 4BS | 3BS | 5D |
| 12 | ½ | 1 | 5D | 5D | 4BS | 3BS | 2SB | 4BS |
| 12 | ¼ | 2B | 3BS | 3BS | 2SB | 2B | 1 | 3B |
| 12 | ¼ | 1 | 3BS | 3BS | 2B | 2B | 1 | 3B |
| 12 | ⅛ | 1 | 3BS | 3BS | 2S | 2SB | 1 | 2B |

EXAMPLE 14

Evaluation of Compounds as Insecticides

In this evaluation, each compound to be tested was dissolved in a 1:1 mixture of acetone and ethanol containing a small amount of Toximul R and Toximul S (each a sulfonate/nonionic blend produced by Stephan Chemical Company, Northfield, Ill.). The solution was then diluted with distilled water to a concentration of 1000 ppm of test compound. Lesser concentration formulations were made by diluting a portion of the 1000 ppm solution with distilled water containing 225 mg. of Toximul R and 125 mg. of Toximul S per liter.

Evaluations were made on Mexican bean beetle (*Epilachna varivestis*), Southern armyworm (*Prodenia eridania*), two-spotted spider mite (*Tetranychus urticae*), and housefly (*Musca domestica*). Test methods for each species were as follows.

Mexican Bean Beetle

This test was conducted with second instar larvae of *Epilachna varivestis* Mulsant, order Coleoptera, family Coccinellidae. Larvae for the test, of uniform size and not molting, were picked by hand from flats of Bountiful snap beans on which they were grown and were placed in 100×20 mm plastic petri dishes for testing. Five larvae were used per replicate.

Two 4- to 6-day-old Bountiful green bean primry leaves (approximately 6 sq. in. of leaf surface) were used for each replicate. Two replicates were run per compound.

Tops and bottoms of the leaves were sprayed to wetting with about 8-10 ml. of the test formulation containing 1000 ppm (0.1%) of the test compound. Spraying was done with a DeVilbis special atomizer No. 5004, with a No. 631 cut-off, constructed by the DeVilbiss Company, Toledo, Ohio. The nozzle of the atomizer was held 12 to 18 inches from the leaves and was supplied with 5-6 psi air pressure. The atomizer was rinsed with acetone after each compound was sprayed. The plants were allowed to dry. The leaves were then cut from the plants and placed in the petri dishes containing the bean beetle larvae. A small wad of wet cellucotton was added to each dish to help prevent the leaves from wilting.

Two leaves were sprayed with 5 ml. of a formulation containing 500 ppm (0.05%) Malathion [0,0-dimethyl-S-(1,2-dicarbethoxyethyl)dithiophosphate] as the reference standard. Two leaves were sprayed with a formulation made up of water, solvent, and emulsifier to be used as the negative control. Two leaves were held as untreated controls.

After 4 days, a mortality count was made and the amount of feeding was noted. Moribund larvae were counted as dead. In case of a question whether a larva was alive or moribund, it was probed with a needle, and if it showed considerable movement, it was called alive.

Southern Armyworm Test

This test was conducted with second to third instar larvae of *Spodoptera eridania* Cramer, Order Lepidoptera, Family Noctuidae. Uniform larvae (3rd instar) about 1 to 1.2 cm. in length were picked by hand from flats of Henderson lima beans and placed in plastic petri dishes.

The procedure otherwise was the same as used with the Mexican bean beetle reported above, except that 5 ml. of a formulation containing 100 ppm (0.01%) DDT [1,1,1-trichloro-2,2-bis(p-chlorophenyl)ethane] was used as the reference standard.

Two-spotted Spider Mite Test

This test was conducted with nymphs and adults of *Tetranychus urticae* (Koch), Order Acarina, Family Tetranychidae.

This test was run using blue hubbard squash plants which were grown in vermiculite (insulation grade No. 1) in 5 oz. plastic Dixie cups. One cotyledon is removed from each plant to remain in the cups. On retests two plants were left in each cup and on regular initial tests one plant was left in each cup. Each cotyledon is infested by placing a mite infested trifoliate bean leaf on if. Infected plants in cups were held for one day, then sprayed to wetting with formulations containing 1000 ppm of the test compound, using the DeVilbiss atomizer with 5-6 psi air pressure. Retests were run at 100 ppm. Tests were read four days after treatment. Two unsprayed but infested plants were held as a control. Two infested plants were sprayed with a formulation containing 750 ppm of galecron [N'-(4-chloro-o-tolyl)-N,N-dimethylformamidine monohydrochloride] as a reference standard.

House Fly Contact Test

This test was conducted with 4-day-old adults of *Musca domestica* (Linne), Order Diptera, Family Muscidae.

Rearing cages of 4-day-old adult house flies were placed in a cold room and held for one hour at 35° to 40° F. to chill so that the flies could be transferred to test cages. Approximately 100 flies were transferred to each test cage using a small scoop. The stainless steel test cages were five inches in diameter and one and three-fourths inches deep with a stainless steel screen bottom and screened removable friction fitting lid. The small hole on the side of the cage was kept stoppered except when a wick was inserted for feeding and watering.

Each cage was sprayed with 5 ml. of the test formulation containing 1000 ppm. of the test compound, using a DeVilbiss atomizer supplied with 5 psi air pressure. The nozzle was 33 inches from the top of the cage. After spraying, cages were allowed to dry.

Knockdown counts were made two hours after spraying and then the flies were fed and watered by inserting a four-inch wick of Fibre Flex Supreme, unbleached (16/32"), (manufactured by Sackner Products, Inc., Grand Rapids, Mich.) in the hole on the side of the cage. The cage was placed so that the wick hung down into a pan of five percent sugar solution in water.

One replicate was run for each test compound. One unsprayed cage was held as a control, one cage was sprayed as a negative control, and one cage was sprayed with a formulation containing 50 ppm. (0.005%) DDT as a reference standard.

Mortality counts were made 24 hours after spraying. The cage was rapped lightly. All flies that did not fly or walk up from the bottom of the cage were considered dead or moribund. Moribund flies were counted as dead.

For all of the test species, the following rating system was used:

| Rating | % Dead |
| --- | --- |
| 0 | 0 |
| 1 | 1-50 |
| 2 | 51-99 |
| 3 | 100 |

When less than half of the leaves were eaten, percent feeding was recorded as follows:

| Rating | |
| --- | --- |
| 0 | none of the leaves eaten |
| 1 | 1-50% of the leaves eaten |

| | | MITE-INSECT SCREEN | | | |
| --- | --- | --- | --- | --- | --- |
| Compound of Example No. | Rate In ppm. | Mexican Bean Beetle Stom./Feed. | Southern Armyworm Stom./Feed. | 2-Sp. Spider Mite Cont. | Housefly Cont./Kd. |
| 2 | 1000 | 3   0 | 0   — | 3 | —   — |
| | | 3   1 | 0   — | — | —   — |
| 2 | 1000 | 3   — | —   — | 3 | 3   1 |
| | | 3   — | —   — | 3 | —   — |
| 2 | 100 | 3   0 | —   — | 3 | —   — |
| | | 3   0 | —   — | 3 | —   — |
| 5 | 1000 | 3   — | 3   1 | 3 | —   — |
| | | 3   — | 2   1 | — | —   — |

-continued

| Compound of Example No. | Rate In ppm. | MITE-INSECT SCREEN | | | | | |
|---|---|---|---|---|---|---|---|
| | | Mexican Bean Beetle Stom./Feed. | | Southern Armyworm Stom./Feed. | | 2-Sp. Spider Mite Cont. | Housefly Cont./Kd. |
| 12 | 1000 | 3 | 1 | 0 | — | 3 | 2 0 |
| | | 3 | 0 | 0 | — | — | — — |

Although the compounds of the present invention exhibit herbicidal and insecticidal activity, as discussed above, the compounds can also be employed for their ectoparasiticidal activity. In this use, the compounds are administered to warm blooded host animals to control insects and acarina parasites on the host animals. The compounds permeate the body of the host animals, so that parasites feeding thereon consume a toxicant amount of the compound and are thereby controlled.

Parasitic insect and acarina are legion and include species which are bloodsucking as well as flesh eating, and species which are parasitic during all of their life cycle or only part of their life cycle, such as only the larval or only the adult stage. Representative species include the following:

| Parasites of Horses | |
|---|---|
| horsefly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| common horse bot fly | Gasterophilus intestinalis |
| chin fly larva | Gasterophilus nasalis |
| nose bot fly larva | Gasterophilus haemorrhoidalis |
| uz,3/13 Parasites of Bovines | |
| horn fly | Haematobia irritans |
| cattle biting louse | Bovicola bovis |
| short-nosed cattle louse | Haematopinus eurysternus |
| long-nosed cattle louse | Linognathus vituli |
| tsetse fly | Glossina spp. |
| stable fly | Stomoxys calcitrans |
| horse fly | Iabanus spp. |
| cattle follicle mite | Demodex bovis |
| scab mite | Psoroptes ovis |
| cattle tick | Boophilus microplus |
| Gulf Coast tick | Amblyomma maculatum |
| Lone-Star tick | Ambylomma americanum |
| ear tick | Otobius megnini |
| Rocky Mountain spotted fever tick | Dermacentor andersoni |
| heel fly | Hypoderma lineatum |
| bomb fly | Hypoderma bovis |
| blowfly larva | Callitroga hominivorax |
| assassin bug | Reduvius spp. |
| mosquito | Culiseta inornata |
| Parasites of Swine | |
| hog louse | Haematopinus suis |
| chigoe flea | Dermatophilus penetrans |
| Parasites of Sheep and Goats | |
| bloodsucking body louse | Haematopinus ovillus |
| bloodsucking foot louse | Linognathus pedalis |
| sheep ked | Melophagus ovinus |
| sheep scab mite | Psoroptes ovis |
| nose bot fly | Oestrus ovis |
| greenbottle fly | Lucilia sericata |
| black blowfly | Phormia regina |
| secondary screw-worm | Callitroga macellaria |
| Parasites of Poultry | |
| bed bug | Cimex lectularius |
| Southern chicken flea | Echidnophaga gallinacea |
| fowl tick | Argas persicus |
| chicken mite | Dermanyssus gallinae |
| scaly-leg mite | Knemidokoptes mutans |
| depluming mite | Knemidokoptes gallinae |
| Parasites of Dogs | |

-continued

| | |
|---|---|
| horse fly | Tabanus spp. |
| stable fly | Stomoxys calcitrans |
| mange mite | Sarcoptes scabiei |
| dog follicle mite | Demodex canis |
| dog flea | Ctenocephalis canis |
| American dog tick | Dermacentor variabilis |
| brown dog tick | Rhipicephalus sanguineus |

Although the parasites are listed above as associated with a particular host, in fact the various parasites freely attack other animals as well.

The rate, timing, and manner of effective administration will vary widely. The compounds can be administered over the entire lifespan of the host, or for only a peak season of parasitic attack. In general, effective parasite control is achieved at rates of from 0.1 to about 15 mg./kg., preferably from about 1.0 to about 10. Optimum rates are often from 5 to 7.5 mg./kg.

The compounds can be employed as such but are more typically formulated to facilitate administration to host animals. The compounds are formulated with a physiologically acceptable adjuvant, which can be any substance that aids in the implementation of the ectoparasiticidal activity of the compounds of the present invention. The adjuvant can be a solvent, an inert diluent, a surface active agent, a suspending agent, and the like. The compounds can be formulated for oral administration in the usual forms, such as drenches, tablets, capsules. The compounds can also be formulated as an injectable solution or suspension, for subcutaneous, dermal, intraperitoneal, intramuscular, or intravenous injection. In some applications, the compounds are conveniently formulated as one component of a standard animal feed. In this embodiment, it is usual to formulate the present compound first as a premix in which the compound is dispersed in a liquid or particulate solid carrier. The premix can contain from 2 to 10 grams of compound per pound. The premix is in turn formulated into the ultimate feed by conventional mixing.

Since ectoparasitic attack generally takes place during a substantial portion of the host animal's lifespan, it is preferred to administer the compounds of the present invention in a form to provide sustained release over a period of time. Conventional procedures include the use of a matrix which physically inhibits dissolution, where the matrix is a waxy semisolid such as the vegetable waxes or a high molecular weight polyethylene glycol. Sustained release of the compounds of the present invention can also be achieved by the use of an implant such as from a silicone-containing rubber.

The compounds of the present invention can also be formulated in a copolymeric matrix, such as that derived from about 60 to about 95 percent of lactic acid and about 40 to about 5 percent of glycolic acid.

Such copolymers are prepared by condensation of lactic acid and glycolic acid in the presence of a readily removable polymerization catalyst. Such catalysts include strong acid ion-exchange resins in the form of beads or similarly hard structures which are easily removed by filtration or similar techniques. Particularly preferred polymerization catalysts include commercially available strong acid ion-exchange resins such as Amberlite IR-118(H), Dowex HCR-W (formerly Dowex 50W), Duolite C-20, Amberlyst 15, Dowex MSC-1, Duolite C-25D, Duolite ES- 26 and related strong acid ion-exchange resins. The catalyst is added to a mixture of about 60 to about 95 parts by weight of lactic acid and about 40 to about 5 parts by weight of glycolic acid. The amount of catalyst utilized is not critical to the polymerization, but typically is from about 0.01 to about 20.0 parts by weight relative to the total weight of combined lactic acid and glycolic acid. The polymerization generally is carried out in the absence of solvents; however, organic solvents such as dimethylsulfoxide or N,N-dimethylformamide can be utilized if desired. The polymerization reaction routinely is carried out in a reaction system equipped with a condensing system, thereby permitting the collection and removal of water that is formed, as well as facilitating the removal of any lactide and glycolide by-products that are formed. The polymerization reaction generally is conducted at an elevated temperature of about 100° to about 250° C., and at such temperature is usually substantially complete within about 3 to about 172 hours, normally about 48 to about 96 hours. Ideally, the reaction can be carried out under a reduced pressure, thereby further facilitating removal of water and by-products.

The copolymer thus formed is readily recovered by simply filtering the molten reaction mixture, for example through a wire screen, to remove substantially all of the strong acid ion-exchange polymerization catalyst. Alternatively, the reaction mixture can be cooled to room temperature and then dissolved in a suitable organic solvent such as dichloromethane or acetone and then filtered by normal means so as to remove the solvent-insoluble strong acid ion-exchange resin. The copolymer then is isolated by removal of the solvent from the filtrate, for instance by evaporation under reduced pressure. Further purification of the copolymer can be accomplished if desired by re-dissolving it in a suitable organic solvent and further filtration, including the use of standard filter aids if desired.

Copolymers prepared by the foregoing process generally have an inherent viscosity when measured in chloroform of about 0.08 to about 0.30 (measured by standard techniques utilizing an Ubbelohde viscometer in which chloroform has an efflux time of about 51 seconds at 25° C.), and a molecular weight of about 6000 to about 35000. A preferred copolymer is one derived from about 60 to about 90 weight percent of lactic acid and about 40 to about 10 weight percent glycolic acid with an inherent viscosity of about 0.10 to about 0.25. A more preferred copolymer is one derived from about 70 to about 80 weight percent lactic acid and about 30 to about 20 percent glycolic acid, with an inherent viscosity of about 0.13 to about 0.23 and a molecular weight of about 15000 to about 30000.

The present compounds can be formulated with the above described copolymers, or other sustained release agents, in conventional manners. In one method, the copolymer and present compound are dissolved in a suitable organic solvent, which is then removed. The resulting solid mass can be ground and thereafter administered as in, for examples, capsules or other forms for oral administration. In another method, the compound and copolymer are first dissolved in a suitable organic solvent and the solvent thereafter removed. The copolymer/compound formulation is then melted and extruded into rods having a diameter of from about 1.0 to about 10.0 millimeters. The rods can be cut to a length which, implanted in an animal, will provide the desired ectoparasitic dose of compound over a sustained period. Formulations of the present compound with the copolymers described above can also contain other adjuvants to facilitate the use of the compounds as veterinary substances.

EXAMPLE 15

Evaluation of Representative Compounds in Guinea Pigs

Representative compounds of the present invention were evaluated against larvae of blowfly (*Phormia regina*) and against adult housefly (*Musca domestica*). In these evaluations, the candidate compound was administered to each of two male guinea pigs weighing from about 400 grams to about 1000 grams. Administration was via the intraperitoneal route, the compound having been formulated in sesame oil. At twenty-four hours following administration of the compound, blood was withdrawn from the guinea pigs. The serum portion was isolated and blowfly larvae and adult houseflies were fed on the serum. For the blowfly assay, 10 ml. of serum were placed in a test tube with a wick onto which 50 blowfly larvae were placed. The covered test tube was incubated at 27° C. for 24 hours, at which time efficacy of the candidate compound was determined as the percent mortality of the blowfly larvae, adjusted by normal mortality in a control, and reported according to the following rating scale:

| Rating | | % Mortality |
|---|---|---|
| 0 | = | none dead |
| 1 | = | <50% dead |
| 2 | = | 51–75% dead |
| 3 | = | 76–90% dead |
| 4 | = | 91–99% dead |
| 5 | = | 100% dead |

Percent mortality was determined separately for each guinea pig.

For the adult housefly test, 10 ml. of serum were employed to saturate a wick which was placed in a petri dish. Twenty-five chilled houseflies were placed in the dish which was then incubated for 24 hours at 27° C. and 50% relative humidity. After the end of the twenty-four hours, the efficacy of the candidate compound was determined as the percent mortality of housefly, adjusted as for blowfly by normal mortality in a control and reported according to the same scale as above.

| | | Efficacy Rating | |
|---|---|---|---|
| Compound of Example No. | Dose in mg./kg. | Blowfly Larvae | Adult Housefly |
| 7 | 50 | At each dose, both | |
| | 25 | guinea pigs died. | |
| | 10 | 0 | 1 |
| | 10 | 5 | 5 |
| 6 | 10 | 5 | 5 |
| | 10 | 5 | 5 |
| | 5 | 5 | 5 |
| | 5 | Guinea pig died | |
| 4 | 10 | Both guinea pigs died. | |
| | 5 | 5 | 5 |

-continued

| Compound of Example No. | Dose in mg./kg. | Efficacy Rating | |
|---|---|---|---|
| | | Blowfly Larvae | Adult Housefly |
| 5 | 5 | 5 | 5 |
| | 5 | 0 | 1 |
| | 5 | 0 | 1 |
| | 1 | 0 | 1 |
| | 1 | 0 | 1 |
| 8 | 20 | Both guinea pigs died. | |
| | 5 | 5 | 5 |
| | 5 | 5 | 5 |

EXAMPLE 16

Evaluation of 2-Hydroxy-2,6-Bis(Trifluoromethyl)-4-Nitrobenzimidazoline, Sodium Salt, Administered to Calf by Intramuscular Injection For this evaluation a male calf weighing 230 kilograms was employed. The compound of Example 3, 2-hydroxy-2,6-bis(trifluoromethyl)-4-nitrobenzimidazoline, sodium salt, was administered by intramuscular injection in the loin area; the compound was formulated in water, 11.50 mg. (5 mg./kg.) a total volume of 2.5 ml.

The calf was observed thereafter and regular determinations made of the efficacy of the treatment against blowfly larvae and adult housefly. Efficacy was assayed in the manner described in the preceding example. Regular determinations were also made of the concentration of the compound in the blood. A control animal, a male calf weighing 128 kilograms, was also maintained, and blood concentrations and efficacy determinations made as for the treated animal. Results were as described in the following table.

| Animal | Day/ Hours From Beginning of Test | PPM Blood Residue | Efficacy (expressed in terms of alive/dead) | | | |
|---|---|---|---|---|---|---|
| | | | 6-Hour Reading | | 24-Hour Reading | |
| | | | Adult House-fly | Blow-fly Larvae | Adult House-fly | Blow-fly Larvae |
| Test | 0/0 | 0 | — | — | 29/1 | 40/0 |
| Test | 0/6 | 18.2 | 28/2 | 0.50 | 0/30 | 0/50 |
| Test | 0/12 | 35.5 | 27/3 | 0/45 | 0/30 | 0/45 |
| Control | 0/12 | 0 | — | — | — | — |
| Test | 0/18 | 45/8 | 24/6 | 0/40 | 0/30 | 0/40 |
| Control | 0/18 | 0 | — | — | — | — |
| Test | 1/0 | 32.9 | — | — | 0/33 | 0/50 |
| Control | 1/0 | 0 | 30/0 | — | 30/0 | 50/0 |
| Test | 2/0 | 28.6 | — | — | 0.27 | 0/50 |
| Control | 2/0 | 0 | 30/0 | — | 24/6 | 40/6 |
| Test | 3/0 | 23/3 | — | — | 0/26 | 0/50 |
| Control | 3/0 | — | 30/0 | 35/0 | 30/0 | 35/0 |
| Test | 4/0 | 12.0 | — | — | 0/29 | 0/50 |
| Control | 4/0 | 0 | 35/0 | 30/0 | 35/0 | 30/0 |
| Test | 5/0 | 15.0 | — | — | 0/26 | 0/45 |
| Control | 5/0 | 0 | 25/0 | 30/0 | 25/0 | 30/0 |
| Test | 6/0 | 12.2 | 24/6 | — | 0.30 | 0/50 |
| Control | 6/0 | 0 | 30/0 | 35/0 | 27/3 | 35/0 |
| Test | 7/0 | 8.9 | 30/0 | — | 2/20 | 4/51 |
| Control | 7/0 | 0 | 30/0 | — | 30/0 | 35/0 |
| Test | 8/0 | 6.6 | 25/0 | — | 5/23 | 5/40 |
| Control | 8/0 | 0 | 25/0 | — | 24/1 | 35/0 |
| Test | 9/0 | 5.2 | 25/0 | — | 2/19 | 5/45 |
| Control | 9/0 | 0 | 30/0 | — | 30/0 | 35/0 |
| Test | 10/0 | 5.9 | 27/0 | — | 1/18 | 5/45 |
| Control | 10/0 | 0 | 25/0 | — | 23/2 | 30/0 |
| Test | 11/0 | 5.0 | 25/0 | — | 3/22 | 5/30 |
| Control | 11/0 | 0 | 30/0 | — | 25/5 | 30/0 |
| Test | 12/0 | 3.5 | — | — | 5/21 | 10/40 |
| Control | 12/0 | 0 | — | — | 35/0 | 40/0 |
| Test | 13/0 | 2.1 | — | — | 10/15 | 40/0 |
| Control | 13/0 | 0 | — | — | 28/2 | 40/0 |
| Test | 14/0 | 1.8 | — | — | 13/10 | 40/0 |
| Control | 14/0 | 0 | — | — | — | — |
| Test | 15/0 | 2.3 | — | — | 13/12 | 40/0 |
| Control | 15/0 | 0 | — | — | — | — |
| Test | 16/0 | 1.8 | — | — | 13/11 | 40/0 |
| Control | 16/0 | 0 | — | — | — | — |
| Test | 17/0 | 1.6 | — | — | 13/10 | 40/0 |
| Control | 17/0 | 0 | — | — | 46/9 | 40/0 |
| Test | 18/0 | 1.0 | — | — | 15/9 | 40/0 |
| Control | 18/0 | 0 | — | — | 33/0 | 40/0 |

EXAMPLE 17

Evaluation of 2-Hydroxy-2-(1,1,2,2-Tetrafluoroethyl)-4-Nitro-6-(Trifluoromethyl)Benzimidazoline, Sodium Salt, Administered To Calves By Intravenous Injection A group of three calves each weighing about 220 kilograms was employed. The compound of Example 2, 2-hydroxy-2-(1,1,2,2-tetrafluoroethyl)-4-nitro-6-(trifluoromethyl)benzimidazoline, sodium salt, was dissolved in distilled water and the resulting solution was administered by intravenous injection. Rates of administration increased throughout the evaluation period, from 0.5 to 1.5 mg./kg. of body weight, with each dose supplied for a period of 5 days (except the 1.5 mg./kg. dose, which was administered for 6 days).

On each day of the evaluation, immediately preceding that day's injection, a sample of blood was withdrawn from each calf. The concentration of the compound in the blood was determined; and the efficacy of the compound against adult housefly and blowfly larvae was assayed by the method described in Example 15. Efficacy was reported, however, as the percent of blowfly larvae or adult housefly which was killed. On some days, blood samples were withdrawn at various periods of time post-injection, and additional blood determinations made. The results were as follows.

| Dose (mg/kg) | Day/minutes post-injection | PPM Blood Residue Animal Number | | | % Efficacy Animal Number | | | | | |
|---|---|---|---|---|---|---|---|---|---|---|
| | | | | | 986 | | 987 | | 991 | |
| | | 986 | 987 | 991 | Adult Housefly | Blowfly Larvae | Adult Housefly | Blowfly Larvae | Adult Housefly | Blowfly Larvae |
| 0.50 | 0 | NDR | NDR | NDR | 0 | 0 | 0 | 0 | 0 | 0 |
| 0.50 | 1 | 1.6 | 1.8 | 2.0 | 50 | 40 | 73 | 33 | 84 | 40 |
| 0.50 | 2 | 2.6 | 2.8 | 3.3 | 100 | 100 | 100 | 100 | 90 | 100 |
| 0.50 | 3 | 3.5 | 3.9 | 4.2 | 100 | 100 | 100 | 100 | 100 | 100 |

-continued

| Dose (mg/kg) | Day/minutes post-injection | PPM Blood Residue Animal Number | | | % Efficacy Animal Number | | | | | |
|---|---|---|---|---|---|---|---|---|---|---|
| | | | | | 986 | | 987 | | 991 | |
| | | 986 | 987 | 991 | Adult Housefly | Blowfly Larvae | Adult Housefly | Blowfly Larvae | Adult Housefly | Blowfly Larvae |
| 0.50 | 4 | 5.1 | 6.0 | 5.6 | 100 | 100 | 100 | 100 | 100 | 100 |
| 0.75 | 5/0 | 4.5 | 4.9 | 5.6 | 100 | 100 | 100 | 100 | 100 | 100 |
| | 5/10 | 9.5 | 10.1 | 9.3 | | | | | | |
| | 5/60 | 9.1 | 8.9 | 9.6 | | | | | | |
| | 5/180 | 8.9 | 8.1 | 8.4 | | | | | | |
| | 5/360 | 9.5 | 8.1 | 8.4 | | | | | | |
| 0.75 | 6/0 | 5.4 | 5.6 | 6.0 | 100 | 100 | 100 | 100 | 100 | 100 |
| | 6/60 | 10.0 | 8.9 | 9.6 | | | | | | |
| 0.75 | 7/0 | 6.3 | 6.7 | 6.6 | 100 | 100 | 100 | 100 | 100 | 100 |
| | 7/60 | 9.9 | 9.9 | 10.1 | | | | | | |
| 0.75 | 8/0 | 6.8 | 8.0 | 7.3 | 100 | 100 | 100 | 100 | 100 | 100 |
| | 8/60 | 12.3 | 10.5 | 10.5 | | | | | | |
| 0.75 | 9/0 | 6.5 | 6.7 | 7.3 | 100 | 100 | 100 | 100 | 100 | 100 |
| | 9/60 | 11.4 | 9.2 | 12.5 | | | | | | |
| 1.0 | 10/0 | 8.7 | 8.3 | 9.9 | 100 | 100 | 100 | 100 | 100 | 100 |
| | 10/10 | 15.2 | 14.3 | 16.8 | | | | | | |
| | 10/60 | 16.5 | 13.5 | 16.1 | | | | | | |
| | 10/180 | 14.6 | 12.8 | 15.0 | | | | | | |
| | 10/360 | 13.6 | 13.3 | 14.6 | | | | | | |
| 1.0 | 11/0 | 10.6 | 9.3 | 11.9 | 100 | 100 | 100 | 100 | 100 | 100 |
| | 11/60 | 17.1 | 15.8 | 17.3 | | | | | | |
| 1.0 | 12/0 | 12.4 | 10.4 | 12.9 | 100 | 100 | 100 | 100 | 100 | 100 |
| | 12/60 | 19.0 | 14.9 | 17.9 | | | | | | |
| 1.0 | 13/0 | 13.8 | 9.8 | 11.7 | 100 | 100 | 100 | 100 | 100 | 100 |
| | 13/60 | 18.6 | 16.7 | 17.4 | | | | | | |
| 1.0 | 14/0 | 13.9 | 10.2 | 11.6 | 100 | 100 | 100 | 100 | 100 | 100 |
| | 14/60 | 20.1 | 16.5 | 17.7 | | | | | | |
| 1.5 | 15/0 | 14.3 | 11.6 | 12.6 | 100 | 100 | 100 | 100 | 100 | 100 |
| | 15/10 | 26.5 | 27.2 | 22.9 | | | | | | |
| | 15/60 | 23.1 | 21.1 | 21.2 | | | | | | |
| | 15/180 | 20.6 | 18.4 | 20.6 | | | | | | |
| | 15/360 | 20.4 | 16.2 | 18.7 | | | | | | |
| 1.5 | 16/0 | 17.1 | 15.6 | 14.6 | 100 | 100 | 100 | 100 | 100 | 100 |
| | 16/60 | 27.4 | 25.6 | 23.9 | | | | | | |
| 1.5 | 17/0 | 20.2 | 16.9 | 15.3 | 100 | 100 | 100 | 100 | 100 | 100 |
| | 17/60 | 28.3 | 25.1 | 24.5 | | | | | | |
| 1.5 | 18/0 | 23.2 | 16.8 | 17.1 | 100 | 100 | 100 | 100 | 100 | 100 |
| | 18/60 | 31.5 | 25.4 | 24.1 | | | | | | |
| 1.5 | 19/0 | 21.6 | 16.5 | 17.8 | 100 | 100 | 100 | 100 | 100 | 100 |
| | 19/60 | 32.4 | 24.3 | 24.2 | | | | | | |
| 1.5 | 20/0 | 22.5 | 17.2 | 17.9 | 100 | 100 | 100 | 100 | 100 | 100 |
| | 20/60 | 28.3 | 25.1 | 28.1 | | | | | | |
| None | 21/0 | 19.8 | 16.2 | 18.1 | 100 | 100 | 100 | 100 | 100 | 100 |
| None | 22/0 | 11.1 | 10.1 | 12.3 | 100 | 100 | 100 | 100 | 100 | 100 |
| None | 23/0 | 6.8 | 5.6 | 7.4 | 80 | 100 | 86 | 100 | 95 | 100 |
| None | 24/0 | 4.1 | 3.7 | 5.2 | 50 | 100 | 38 | 100 | 78 | 100 |
| None | 25/0 | 2.9 | 2.2 | 3.5 | 21 | 60 | 20 | 40 | 55 | 100 |
| None | 26/0 | 1.6 | 1.2 | 2.4 | 34 | 75 | 9 | 0 | 35 | 50 |

EXAMPLE 18

Evaluations of 2-Hydroxy-2-(1,1,2,2-Tetrafluoroethyl)-4-Nitro-6-(Trifluoromethyl)Benzimidazoline, Sodium Salt, Administered To Calves By Jugular Infusion Three evaluations were conducted sequentially with the compound of Example 2, 2-hydroxy-2-(1,1,2,2-tetrafluoroethyl)-4-nitro-6-(trifluoromethyl)benzimidazoline, sodium salt, administered daily to calves by jugular infusion of a solution of the compound in distilled water. As described in the preceding example, blood samples were withdrawn and analyzed for concentration of the compound and efficacy against adult housefly and blowfly larvae. Results were as set forth in the following tables.

| | EVALUATION I Concentration in Blood & % Efficacy | | | | | | | |
|---|---|---|---|---|---|---|---|---|
| Day/Hours From Beginning of Test | Animal #988 (141 Kg) Intended Dose, 0.66 mg/kg/day* | | | | Animal #552 (223 Kg) Intended Dose, 0.66 mg/kg/day* | | | |
| | PPM | Adult Housefly | Blowfly Larvae | Actual Dose | PPM | Adult Housefly | Blowfly Larvae | Actual Dose |
| 0 | 0.0 | 5 | 0 | | 0.0 | 16 | 0 | |
| 0/1 | 0.0 | 5 | 0 | | 0.0 | 9 | 0 | |
| 0/2 | 0.3 | 10 | 0 | | 0.3 | 13 | 0 | |
| 0/4 | 0.6 | 14 | 0 | | 0.6 | 16 | 0 | |
| 0/8 | 1.2 | 40 | 50 | | 1.3 | 33 | 25 | |
| 1/0 | 3.3 | 100 | 100 | .69 | 3.2 | 100 | 100 | .69 |
| 1/8 | 3.5 | 100 | 100 | | 4.0 | 100 | 100 | |

EVALUATION I
Concentration in Blood & % Efficacy

| Day/Hours From Beginning of Test | Animal #988 (141 Kg) Intended Dose, 0.66 mg/kg/day* | | | | Animal #552 (223 Kg) Intended Dose, 0.66 mg/kg/day* | | | |
|---|---|---|---|---|---|---|---|---|
| | PPM | Adult Housefly | Blowfly Larvae | Actual Dose | PPM | Adult Housefly | Blowfly Larvae | Actual Dose |
| 2/0 | 4.0 | 100 | 100 | .69 | 5.5 | 100 | 100 | .69 |
| 2/8 | 4.1 | 100 | 100 | | 5.1 | 100 | 100 | |
| 3/0 | 5.3 | 100 | 100 | .69 | 8.2 | 100 | 100 | .68 |
| 4/0 | 6.0 | 100 | 100 | .72 | 10.6 | 100 | 100 | .71 |
| 5/0 | 6.9 | 100 | 100 | .68 | 11.8 | 100 | 100 | .67 |
| 5/8 | 6.8 | 100 | 100 | | 13.4 | 100 | 100 | |
| 6/0 | 7.1 | 100 | 100 | .69 | 15.7 | 100 | 100 | .69 |
| 6/8 | 7.5 | 100 | 100 | | 13.7 | 100 | 100 | |
| 7/0 | 7.6 | 100 | 100 | .70 | 14.2 | 100 | 100 | .70 |
| 7/8 | 6.4 | 100 | 100 | | 14.9 | 100 | 100 | |
| 8/0 | 6.9 | 100 | 100 | .69 | 16.9 | 100 | 100 | .69 |
| 8/8 | 5.7 | 100 | 100 | | 16.2 | 100 | 100 | |
| 9/0 | 5.8 | 100 | 100 | .70 | 16.7 | 100 | 100 | .70 |
| 9/8 | 5.7 | 100 | 100 | | 17.3 | 100 | 100 | |
| 10/0 | 4.8 | 100 | 100 | | 17.3 | 100 | 100 | |
| 11/0** | 3.7 | 100 | 100 | | 15.1 | 100 | 100 | |
| 12/0 | 3.7 | 100 | 100 | | 14.0 | 100 | 100 | |
| 13/0 | 1.6 | 100 | 100 | | 11.3 | 100 | 100 | |

*Animal 988 actually received an average daily dose of 0.697 mg./kg., animal 552, an average daily dose of 0.691 mg./kg.
**Discontinued infusion on Day 10 at a.m.

EVALUATION II
Concentration in Blood & % Efficacy

| Day/Hours from Beginning of Test | Animal #872 (100 Kg.) Intended Dose, 0.66 mg/kg/day* | | | |
|---|---|---|---|---|
| | PPM | Adult Housefly | Blowfly Larvae | Actual Dose |
| 0/0 | NDR | 17 | 0 | |
| 0/2 | NDR | 20 | 0 | |
| 0/4 | 0.4 | 20 | 0 | |
| 0/8 | 0.7 | 25 | 0 | |
| 1/0 | 2.4 | 100 | 100 | .66 |
| 1/8 | 3.6 | 100 | 100 | |
| 2/0 | 4.5 | 100 | 100 | .69 |
| 2/8 | 5.2 | 100 | 100 | |
| 3/0 | 6.7 | 100 | 100 | .67 |
| 3/8 | 6.1 | 100 | 100 | |
| 4/0 | 7.4 | 100 | 100 | .65 |
| 5/0 | 8.1 | 100 | 100 | .62 |
| 6/0 | 8.4 | 100 | 100 | .70 |
| 6/8 | 6.7 | 100 | 100 | |
| 7/0 | 7.0 | 100 | 100 | .68 |
| 7/8 | 7.8 | 100 | 100 | |
| 8/0 | 7.6 | 100 | 100 | .67 |
| 8/8 | 7.4 | 100 | 100 | |
| 9/0 | 8.9 | 100 | 100 | .65 |
| 9/8 | 7.8 | 100 | 100 | |
| 10/0** | 6.2 | 100 | 100 | .66 |
| 11/0 | 4.5 | 100 | 100 | 0 |
| 12/0 | 2.9 | 100 | 100 | 0 |
| 13/0 | 2.0 | 75 | 80 | 0 |
| 14/0 | 1.3 | 39 | 25 | 0 |

*Animal actually received an average daily dose of 0.665 mg./kg.
**Infusion curtailed at end of Day 10.

EVALUATION III
Concentration in Blood & % Efficacy

| Day/Hours From Beginning of Test | Animal #501 (141 Kg) Intended Dose, 0.50 mg/kg/day | | | Animal #502 (223 Kg) Intended Dose, 0.50 mg/kg/day | | |
|---|---|---|---|---|---|---|
| | PPM | Adult Housefly | Blowfly Larvae | PPM | Adult Housefly | Blowfly Larvae |
| 0/0 | NDR | 16 | 0 | NDR | 20 | 0 |
| 0/1 | 0.4 | 5 | 0 | 0.0 | 16 | 0 |
| 0/2 | 0.5 | 5 | 0 | 0.0 | 20 | 0 |
| 0/4 | 0.7 | 24 | 0 | 0.5 | 32 | 0 |
| 0/8 | 0.7 | 27 | 0 | 0.6 | 32 | 0 |
| 1/0 | 1.6 | 36 | 0 | 0.9 | 33 | 0 |
| 2/0 | 3.7 | 100 | 100 | 3.2 | 100 | 100 |
| 3/0 | 4.9 | 100 | 100 | 5.2 | 100 | 100 |
| 3/8 | 4.0 | 100 | 100 | 5.2 | 100 | 100 |
| 4/0 | 4.8 | 100 | 100 | 6.6 | 100 | 100 |
| 4/8 | 4.4 | 100 | 100 | 6.0 | 100 | 100 |
| 5/0 | 4.1 | 100 | 100 | 7.3 | 100 | 100 |
| 5/8 | 3.6 | 100 | 100 | 6.9 | 100 | 100 |
| 6/0 | 3.6 | 100 | 100 | 7.9 | 100 | 100 |
| 6/8 | 2.0 | 100 | 100 | 6.3 | 100 | 100 |
| 7/0 | 1.7 | 100 | 100 | 7.3 | 100 | 100 |
| 7/8 | 2.6 | 100 | 100 | 9.6 | 100 | 100 |
| 8/0 | 2.5 | 100 | 100 | 7.5 | 100 | 100 |
| 9/0 | 2.6 | 100 | 100 | 6.3 | 100 | 100 |
| 10/0 | 2.5 | 100 | 100 | 4.4 | 100 | 100 |
| 10/8* | 2.0 | 100 | 100 | 4.3 | 100 | 100 |
| 11/0 | 1.8 | 43 | 100 | 3.8 | 100 | 100 |
| 12/0 | 0.8 | 30 | 0 | 2.8 | 75 | 75 |
| 13/0 | 0.5 | 20 | 0 | 2.0 | 75 | 63 |
| 14/0 | NDR | 33 | 25 | 1.7 | 25 | 25 |
| 15/0 | 0.3 | 27 | 25 | 1.4 | 29 | 25 |
| 16/0 | NDR | 19 | 0 | 1.3 | 36 | 25 |
| 17/0 | NDR | 31 | 25 | 1.2 | 25 | 20 |
| 18/0 | NDR | 23 | 0 | 0.9 | 22 | 0 |
| 19 | | 18 | 20 | | 22 | 20 |
| | | 21 | 0 | | | |
| | | 20 | 0 | | | |

*Infusion treatment ended for all calves except calf no. 988 on day 10 Treatment for calf no. 988 ended on day 15. Adjustment made because calf no. 988 chewed out tubes on day 2, 3 and 4.

| Day/Hours From Beginning of Test | Animal #002 (196 Kg) Intended Dose, 0.25 mg/kg/day | | | Animal #988 (196 Kg) Intended Dose, 0.25 mg/kg/day | | |
|---|---|---|---|---|---|---|
| | PPM | Adult Housefly | Blowfly Larvae | PPM | Adult Housefly | Blowfly Larvae |
| 0/0 | NDR | 16 | 0 | NDR | 15 | 0 |
| 0/1 | 0.0 | 22 | 0 | 0.0 | 27 | 0 |
| 0/2 | 0.0 | 22 | 0 | 0.0 | 22 | 0 |
| 0/4 | 0.0 | 16 | 0 | 0.0 | 25 | 0 |
| 0/8 | 16 | 0 | 0.0 | 13 | 0 | |
| 1/0 | 0.9 | 23 | 0 | 1.0 | 25 | 0 |
| 2/0 | 2.0 | 100 | 100 | 0.9 | 50 | 75 |
| 3/0 | 2.3 | 100 | 100 | 1.5 | 75 | 75 |
| 3/8 | 2.6 | 100 | 100 | 1.5 | 59 | 75 |
| 4/0 | 2.9 | 90 | 100 | 1.3 | 56 | 70 |
| 4/8 | 3.1 | 100 | 100 | 1.1 | 56 | 70 |

EVALUATION III
Concentration in Blood & % Efficacy

| | | | | | | |
|---|---|---|---|---|---|---|
| 5/0 | 3.6 | 100 | 100 | 1.8 | 50 | 50 |
| 5/8 | 4.0 | 100 | 100 | 2.1 | 58 | 60 |
| 6/0 | 4.3 | 100 | 100 | 2.1 | 63 | 60 |
| 6/8 | 3.3 | 100 | 100 | 2.5 | 100 | 100 |
| 7/0 | 3.1 | 100 | 100 | .5.7 | 100 | 100 |
| 7/8 | 4.2 | 100 | 100 | 3.1 | 100 | 100 |
| 8/0 | 4.9 | 100 | 100 | 3.5 | 100 | 100 |
| 9/0 | 5.1** | 100 | 100 | 4.2 | 100 | 100 |
| 10/0 | 3.6 | 100 | 100 | 5.3 | 100 | 100 |
| 10/8 | 3.2*** | 100 | 100 | 4.7 | 100 | 100 |
| 11/0 | 2.8 | 100 | 100 | 5.0 | 100 | 100 |
| 12/0 | 2.5 | 55 | 50 | 5.2 | 100 | 100 |
| 13/0 | 1.6 | 66 | 75 | 4.4 | 100 | 100 |

**Calf 002 infusion tube displaced for approximately 12 hours.
***Infusion curtailed at end of Day 10.

| | | | | | | |
|---|---|---|---|---|---|---|
| 14/0 | 1.7 | 27 | 20 | 4.8 | 100 | 100 |
| 15/0 | 1.3 | 33 | 25 | 3.5*** | 100 | 100 |
| 16/0 | 1.2 | 24 | 0 | 2.2 | 66 | 55 |
| 17/0 | 0.9 | 22 | 0 | 1.5 | 27 | 20 |
| 18/0 | 0.8 | 20 | 0 | 0.8 | 14 | 0 |
| 19 | | 19 | 0 | | 13 | 0 |
| 20 | | | | | 21 | 0 |
| 21 | | | | | 21 | 0 |

***Infusion curtailed at end of Day 15.

EXAMPLE 19

Evaluation of 2-Hydroxy-2,6-Bis(trifluoromethyl)-4-Nitrobenzimidazoline, Sodium Salt, Administered to Calf Subcutaneously in Pellets The compound of Example 3, 2-hydroxy-2,6-bis(trifluoromethyl)-4-nitrobenzimidazoline, sodium salt was evaluated as an ectoparasiticide when administered as pellets implanted in the ear of a calf numbered animal 106. The compound was formulated neat, in tablets about ⅛" thick. A total of 14 pellets was inserted into the left ear of a 215-kilogram calf, to supply a dose of about 5 mg./kg. Some swelling was noted at 6 hours and 1 day post-insertion. Two other calves received intramuscular injections of aqueous solutions of 2-hydroxy-2,6-bis(trifluoromethyl)-4-nitrobenzimidazoline, sodium salt, to provide 5 or 7.5 mg./kg. of animal body weight. (animals 119 and 121 respectively). Calf 121 was found dead on day 2; another calf, number 123, was treated on day 7 with an intramuscular injection of an aqueous solution of 2-hydroxy-2,6-bis(trifluoromethyl)-4-nitrobenzimidazoline, sodium salt and thereafter maintained throughout the test period. A control animal was also maintained throughout the test period.

Blood samples were taken periodically and analyzed for concentration of the compound in blood and ectoparasiticidal efficacy, as in prior examples. The results were as reported in the following table.

| Day/Hours From Beginning of Test | Animal | PPM Blood Residue | Efficacy (expressed in terms of alive/dead) | | | |
|---|---|---|---|---|---|---|
| | | | 6-hour reading | | 24-hour reading | |
| | | | Adult Housefly | Blowfly Larvae | Adult Housefly | Blowfly Larvae |
| 00 | 106 | 0 | 40/0 | — | 35/5 | 50/0 |
| | 119 | 0 | 32/0 | — | 25/7 | 45/0 |
| | 121 | 0 | 40/0 | — | 25/15 | 50/0 |
| | control | 0 | 35/0 | — | 30/5 | 45/0 |
| 1/0 | 106 | 9.2 | 40/0 | — | 1/39 | 10/55 |
| | 119 | 40.6 | 10/20 | 0/50 | 0/30 | 0/50 |
| | 121 | 64.7 | 0/35 | 0/50 | 0/35 | 0/50 |
| | control | 0 | 35/0 | — | 30/5 | 40/0 |
| 1/6 | 121 | 51.9 | 5/25 | 0/50 | 0/30 | 0/50 |
| 2/0 | 106 | 6.6 | 25/5 | — | 0/30 | 10/65 |
| | 119 | 37.3 | 13/27 | 8/42 | 0/40 | 0/50 |
| | control | 0 | 32/0 | — | 27/5 | 60/0 |
| 3/0 | 106 | 4.1 | 25/0 | — | 3/22 | 15/60 |
| | 119 | 28.9 | 25/5 | 55/10 | 0/30 | 0/65 |
| | control | 0 | 30/0 | — | 25/5 | 65/0 |
| 4/0 | 106 | 6.9 | 25/0 | — | 5/20 | 5/50 |
| | 119 | 25.6 | 18/12 | — | 0/30 | 0/50 |
| | control | 0 | 30/0 | — | 25/5 | 0/50 |
| 5/0 | 106 | 2.7 | 26/0 | — | 6/20 | 35/0 |
| | 119 | 20.9 | 14/8 | 0/40 | 0/22 | 0/40 |
| | control | 0 | 22/0 | — | 15/7 | 0/50 |
| 6/0 | 106 | 4.2 | 35/0 | — | 12/23 | 30/5 |
| | 119 | 12.1 | 24/8 | 35/0 | 0/32 | 0/35 |
| | control | 0 | 25/0 | — | 18/7 | 50/0 |
| 7/0 | 106 | 4.3 | 33/0 | — | 13/20 | 30/0 |
| | 119 | 13.9 | 33/7 | — | 0/40 | 0/30 |
| | control | 0 | 25/0 | — | 18/7 | 50/0 |
| 8/0 | 106 | 3.4 | 32/0 | — | 15/17 | 40/0 |
| | 119 | 14.8 | 17/10 | 35/0 | 0/27 | 0/35 |
| | 123 | 23.6 | 12/20 | 5/35 | 0/32 | 0/40 |
| | control | — | 30/0 | — | 23/7 | 50/0 |
| 9/0 | 106 | 3.0 | 20/3 | — | 20/3 | 35/0 |
| | 119 | 13.9 | 15/8 | — | 0/23 | 0/45 |
| | 123 | 17.3 | 10/18 | 0/35 | 0/28 | 0/35 |
| | control | 0 | 22/0 | — | 17/5 | 50/0 |
| 10/0 | 106 | 2.5 | 24/0 | — | 16/8 | 30/0 |
| | 119 | 10.0 | 24/0 | — | 0/24 | 0/45 |
| | 123 | 12.5 | 21/4 | — | 0/25 | 0/45 |
| | control | 0 | 24/0 | — | 19/5 | 50/0 |
| 11/0 | 106 | 2.2 | 27/0 | — | 20/7 | 30/0 |
| | 119 | 5.6 | 26/0 | — | 2/24 | 0/30 |
| | 123 | 10.9 | 15/8 | — | 0/23 | 6/24 |
| | control | 0 | 28/0 | — | 23/5 | 30/0 |
| 12/0 | 106 | 1.7 | 30/0 | — | 21/9 | 30/0 |
| | 119 | 7.3 | 27/0 | — | 2/25 | 30/0 |
| | 123 | 8.1 | 27/3 | — | 0/30 | 27/3 |
| | control | 0 | 28/0 | — | 23/5 | 30/0 |
| 13/0 | 106 | 1.5 | 31/0 | — | 16/15 | 30/0 |
| | 119 | 5.6 | 22/0 | — | 2/20 | 30/0 |
| | 123 | 7.5 | 20/0 | — | 0/20 | 30/0 |
| | control | 0 | 28/0 | — | 23/5 | 30/0 |
| 14/0 | 106 | 1.4 | 27/0 | — | 19/8 | 30/0 |
| | 119 | 4.9 | 22/0 | — | 3/19 | 30/0 |
| | 123 | 6.5 | 31/1 | — | 2/30 | 30/0 |
| | control | 0 | 28/0 | — | 23/5 | 30/0 |
| 15/0 | 106 | 1.3 | 24/0 | — | 20/4 | 30/0 |
| | 119 | 3.5 | 33/0 | — | 5/28 | 30/0 |
| | 123 | 5.0 | 20/0 | — | 4/16 | 30/0 |
| | control | 0 | 28/0 | — | 23/5 | 30/0 |
| 16/0 | 106 | 1.1 | — | — | 21/8 | 30/0 |
| | 119 | 3.2 | — | — | 6/19 | 30/0 |
| | 123 | 2.2 | — | — | 5/20 | 30/0 |
| | control | 0 | — | — | 20/8 | 30/0 |
| 17/0 | 106 | 0.9 | 30/0 | 35/0 | 24/6 | 35/0 |
| | 119 | 2.3 | 30/0 | 35/0 | 17/10 | 35/0 |
| | 123 | 2.1 | 30/0 | 40/0 | 20/8 | 40/0 |
| | control | 0 | 30/0 | 35/0 | 22/8 | 35/0 |
| 18/0 | 106 | 0.6 | 28/0 | 30/0 | 20/8 | 30/0 |
| | 119 | 1.3 | 27/0 | — | 16/9 | 35/0 |
| | 123 | 1.5 | 25/0 | — | 15/7 | 35/0 |
| | control | 0 | 30/0 | — | 22/8 | 35/0 |
| 19/0 | 106 | 0.6 | 27/0 | 60/0 | 15/12 | 58/2 |
| | 119 | 1.4 | 28/0 | 60/0 | 12/18 | 60/0 |
| | 123 | 1.2 | 26/0 | — | 13/13 | 58/2 |
| | control | 0 | 25/0 | — | 17/8 | 60/0 |
| 20/0 | 106 | 0.4 | 27/0 | — | 12/15 | 60/0 |
| | 119 | 1.1 | 26/0 | — | 12/14 | 60/0 |
| | 123 | 1.2 | 26/0 | — | 18/8 | 60/0 |
| | control | 0 | 25/0 | — | 17/8 | 60/0 |
| 21/0 | 106 | 0.4 | 25/0 | — | 17/8 | 60/0 |
| | 119 | 0.9 | 23/0 | — | 13/10 | 4/2 |
| | 123 | 0.7 | 38/0 | — | 21/17 | 60/0 |
| | control | 0 | 26/0 | — | 18/8 | 60/0 |

-continued

| Day/Hours From Beginning of Test | Animal | PPM Blood Residue | Efficacy (expressed in terms of alive/dead) | | | |
|---|---|---|---|---|---|---|
| | | | 6-hour reading | | 24-hour reading | |
| | | | Adult Housefly | Blowfly Larvae | Adult Housefly | Blowfly Larvae |
| 22/0 | 106 | 0.3 | 25/0 | — | 17/8 | 70/0 |
| | 119 | 1.1 | 27/0 | — | 16/11 | 60/0 |
| | 123 | 0.6 | 27/0 | — | 15/12 | 60/0 |
| | control | 0 | 24/0 | — | 16/8 | 60/0 |

EXAMPLE 20

Evaluation of 2-Hydroxy-2-(1,1,2,2-Tetrafluoroethyl)-4-Nitro-6-(Trifluoromethyl)Benzimidazoline, Sodium Salt, Administered to Calves Subcutaneously in Pellets The compound of Example 2, 2-hydroxy-2-(1,1,2,2-tetrafluoroethyl)-4-nitro-6-(trifluoromethyl)benzimidazoline sodium salt, was formulated neat into tablets, each containing about 85 mg. of compound.

These pellets were implanted in the right shoulder area of two calves, weighing 400 and 373 kilograms respectively, to supply a dose of about 5 mg./kg. (animals #651 and 1511, respectively). Another calf (animal #656) was maintained as a control and two additional calves weighing 336 and 350 kilograms (animals #654 and 655, respectively) received pellets of 2-(1,1,2,2-tetrafluoroethyl)-4-nitro-6-(trifluoromethyl)benzimidazole, to supply a dose of about 5 mg./kg. of compound.

As described in preceding examples, blood samples were withdrawn and analyzed for the concentration of the compound in the blood and percent efficacy against adult housefly and blowfly larvae. Results were as set forth in the following table.

The present compounds are formulated for anticoccidial use in conventional procedures. Typically, for the control of coccidiosis in poultry, the compound is mixed with a suitable excipient to constitute a pre-mix which is adapted to be mixed with various grains or other poultry feed substances to form the ultimate poultry feedstuff containing one or more of the present compounds as anticoccidial agent. The premix excipient can be, for example, soybean mill materials, wheat bran middlings, rice hulls, etc. In general, the ultimate feedstuff desirably contains the present agent in a concentration of from 10 to 100 ppm.

I claim:

1. A compound of the formula

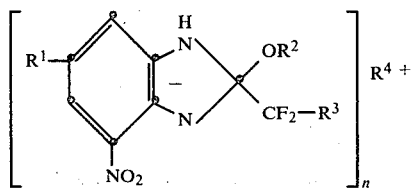

wherein:
R$^1$ represents bromo, chloro, or trifluoromethyl;
R$^2$ represents hydrogen or loweralkyl of C$_1$–C$_4$;
R$^3$ represents hydrogen, fluoro, difluoromethyl, or trifluoromethyl;
R$^4$ represents sodium, potassium, lithium, silver, calcium, ammonium, or substituted ammonium derived from an organic amine which is as basic as, or more basic than, ammonia; and
n represents the valence of R$^4$; or an R$^2$OH solvate thereof.

2. A compound of claim 1 wherein R$^2$ represents hydrogen.

3. A compound of claim 2 wherein R$^1$ represents trifluoromethyl.

4. A compound of claim 3 wherein R$^3$ represents difluoromethyl.

5. The compound of claim 4 which is 2-hydroxy-2-(1,1,2,2-tetrafluoroethyl)-4-nitro-6-(trifluoromethyl)-benzimidazoline, sodium salt or a hydrate thereof.

6. The compound of claim 4 which is 2-hydroxy-2-(1,1,2,2-tetrafluoroethyl)-4-nitro-6-(trifluoromethyl)-benzimidazoline, potassium salt, or a hydrate thereof.

7. The compound of claim 4 which is 2-hydroxy-2-(1,1,2,2-tetrafluoroethyl)-4-nitro-6-(trifluoromethyl)-benzimidazoline, ammonium salt, or a hydrate thereof.

| | Concentration in Blood & % Efficacy | | | | | | | | | | | | | | |
|---|---|---|---|---|---|---|---|---|---|---|---|---|---|---|---|
| | Animal #656 | | | Animal #651 | | | Animal #1511 | | | Animal #655 | | | Animal #654 | | |
| Test Day | PPM | Adult Housefly | Blowfly Larvae | PPM | Adult Housefly | Blowfly Larvae | PPM | Adult Housefly | Blowfly Larvae | PM | Adult Housefly | Blowfly Larvae | PPM | Adult Housefly | Blowfly Larvae |
| 0 | 0.0 | — | — | 0.0 | — | — | 0.0 | — | — | 0.0 | — | — | 0.7 | — | — |
| 1 | 0.0 | — | — | 25.3 | 100 | 100 | 31.0 | 100 | 100 | 8.6 | 100 | 100 | 4.5 | 100 | 100 |
| 2 | 0.0 | — | — | 30.3 | 100 | 100 | 14.0 | 100 | 100 | 11.9 | 100 | 100 | 10.9 | 100 | 100 |
| 3 | 0.0 | — | — | — | — | — | 5.2 | 100 | 100 | 12.1 | 100 | 100 | 6.4 | 100 | 100 |
| 4 | 0.0 | — | — | 12.0 | 100 | 100 | 5.4 | 100 | 100 | 9.4 | 100 | 100 | 7.0 | 100 | 100 |
| 5 | 0.0 | — | — | 9.3 | 100 | 100 | 3.2 | 100 | 100 | 9.8 | 100 | 100 | 9.9 | 100 | 100 |
| 6 | 0.0 | — | — | 11.9 | 100 | 100 | 2.4 | 90 | 78 | 7.7 | 100 | 100 | 10.6 | 100 | 100 |
| 7 | 0.0 | — | — | 3.0 | 98 | 100 | 1.5 | 25 | 0 | 7.2 | 100 | 100 | 8.2 | 100 | 100 |
| 8 | 0.0 | — | — | 0.9 | 65 | 40 | 0.8 | 12 | 0 | 7.5 | 100 | 100 | 7.2 | 100 | 100 |
| 9 | 0.0 | — | — | 1.4 | 12 | 0 | 0.6 | 11 | 0 | 3.7 | 100 | 100 | 3.7 | 100 | 100 |
| 10 | 0.0 | — | — | 0.9 | 22 | 0 | 0.4 | 11 | 0 | 5.1 | 100 | 100 | 5.9 | 100 | 100 |

In addition to the several utilities discussed and exemplified above, the compounds of the present invention also exhibit anticoccidial activity. The compounds can therefore be employed for the control of coccidiosis in ruminants and especially in poultry, including chickens and turkeys. The compounds are employed in the usual manner of anticoccidials. Typically an effective amount of one or more of the compounds is administered in the feedstuff or in the drinking water being supplied to the animals. Administration can also be made by injection, implants, and other routes. Such administration is advantageously continued throughout the lifespan of the poultry to maximize the anticoccidial protection.

8. A compound of claim 3 wherein $R^3$ represents fluoro.

9. The compound of claim 8 which is 2-hydroxy-2,6-bis(trifluoromethyl)-4-nitrobenzimidazoline, sodium salt or a hydrate thereof.

10. A compound of claim 1 wherein $R^2$ represents isopropyl.

11. Method of inhibiting insect and acarina parasites which consume tissues of a warm blooded host animal which comprises administering to the host animal an effective amount of an active agent which is a compound of claim 1.

12. The method of claim 11 employing an active agent wherein $R^2$ represents hydrogen.

13. The method of claim 12 employing an active agent wherein $R^1$ represents trifluoromethyl.

14. The method of claim 13 employing an active agent wherein $R^3$ represents difluoromethyl.

15. The method of claim 14 employing as active agent 2-hydroxy-2-(1,1,2,2-tetrafluoroethyl)-4-nitro-6-(trifluoromethyl)benzimidazoline, sodium salt, or a hydrate thereof.

16. The method of claim 14 employing as active agent 2-hydroxy-2-(1,1,2,2-tetrafluoroethyl)-4-nitro-6-(trifluoromethyl)benzimidazoline, potassium salt, or a hydrate thereof.

17. The method of claim 14 employing as active agent 2-hydroxy-2-(1,1,2,2-tetrafluoroethyl)-4-nitro-6-(trifluoromethyl)benzimidazoline, ammonium salt, or a hydrate thereof.

18. The method of claim 13 employing an active agent wherein $R^3$ represents fluoro.

19. The method of claim 18 employing as active agent 2-hydroxy-2,6-bis(trifluoromethyl)-4-nitrobenzimidazoline, sodium salt or a hydrate thereof.

20. Formulation suitable to be administered to a warm blooded host animal to inhibit insect and acarina parasites of the host animal, comprising an effective amount of an active agent which is a compound of claim 1 and a physiologically acceptable adjuvant.

21. The formulation of claim 20 comprising an active agent wherein $R^2$ represents hydrogen.

22. The formulation of claim 21 comprising an active agent wherein $R^1$ represents trifluoromethyl.

23. The formulation of claim 22 comprising an active agent wherein $R^3$ represents difluoromethyl.

24. The formulation of claim 23 comprising as active agent 2-hydroxy-2-(1,1,2,2-tetrafluoroethyl)-4-nitro-6-(trifluoromethyl)benzimidazoline, sodium salt, or a hydrate thereof.

25. The formulation of claim 23 comprising as active agent 2-hydroxy-2-(1,1,2,2-tetrafluoroethyl)-4-nitro-6-(trifluoromethyl)benzimidazoline, potassium salt, or a hydrate thereof.

26. The formulation of claim 23 comprising as active agent 2-hydroxy-2-(1,1,2,2-tetrafluoroethyl)-4-nitro-6-(trifluoromethyl)benzimidazoline, ammonium salt, or a hydrate thereof.

27. The formulation of claim 22 comprising active agent wherein $R^3$ represents fluoro.

28. The formulation of claim 27 comprising as active agent 2-hydroxy-2,6-bis(trifluoromethyl)-4-nitrobenzimidazoline, sodium salt or a hydrate thereof.

* * * * *